(12) United States Patent
Yamazaki et al.

(10) Patent No.: US 8,305,427 B2
(45) Date of Patent: Nov. 6, 2012

(54) IMAGE PROCESSOR AND ENDOSCOPE APPARATUS

(75) Inventors: Kenji Yamazaki, Hino (JP); Yoshinori Takahashi, Ibaraki (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 1446 days.

(21) Appl. No.: 11/886,830

(22) PCT Filed: Mar. 22, 2006

(86) PCT No.: PCT/JP2006/305709
§ 371 (c)(1),
(2), (4) Date: Sep. 21, 2007

(87) PCT Pub. No.: WO2006/101128
PCT Pub. Date: Sep. 28, 2006

(65) Prior Publication Data
US 2009/0021578 A1    Jan. 22, 2009

(30) Foreign Application Priority Data

Mar. 22, 2005  (JP) .................................. 2005-082544

(51) Int. Cl.
*H04N 13/02* (2006.01)
(52) U.S. Cl. ................. 348/46; 348/43; 348/51
(58) Field of Classification Search .................... 348/43, 348/46, 51
See application file for complete search history.

(56) References Cited

U.S. PATENT DOCUMENTS

| 5,282,030 | A |   | 1/1994  | Nishimura et al. |
|-----------|---|---|---------|------------------|
| 5,535,289 | A |   | 7/1996  | Ito |
| 5,872,597 | A | * | 2/1999  | Yamakage et al. ........ 375/240.16 |
| 6,785,415 | B1| * | 8/2004  | Taguchi et al. ............... 382/173 |
| 6,807,300 | B1| * | 10/2004 | Gindele et al. ............... 382/167 |
| 6,941,323 | B1| * | 9/2005  | Galperin ............................. 1/1 |
| 7,995,855 | B2| * | 8/2011  | Albu et al. .................... 382/260 |
| 2002/0118019 | A1 |   | 8/2002 | Nomura |
| 2006/0093233 | A1 | * | 5/2006 | Kano et al. .................... 382/254 |
| 2007/0252074 | A1 | * | 11/2007 | Ng et al. .................... 250/208.1 |
| 2009/0021578 | A1 | * | 1/2009 | Yamazaki et al. ............. 348/65 |
| 2009/0091614 | A1 | * | 4/2009 | Gono et al. .................... 348/68 |

FOREIGN PATENT DOCUMENTS

| EP | 0 511 400 A1 | 11/1992 |
|----|--------------|---------|
| EP | 0 643 534 A1 | 3/1995 |
| EP | 0 833 501 A2 | 4/1998 |

(Continued)

OTHER PUBLICATIONS

Canadian Official Action dated Dec. 2, 2010.

(Continued)

*Primary Examiner* — Michael Won
(74) *Attorney, Agent, or Firm* — Scully, Scott, Murphy & Presser, PC

(57) ABSTRACT

An image processor includes a filter process circuit for executing a filtering of image data picked up by an image pickup unit with a plurality of spatial filters, a brightness calculation circuit for calculating a brightness in a local area of the image data, a weighting circuit for weighting an output of the filter process circuit in accordance with an output of the filter process circuit and/or an output of the brightness calculation circuit, and an inverse filter process circuit for executing an inverse filter process with respect to an output of the weighting circuit to generate process image data.

24 Claims, 19 Drawing Sheets

FOREIGN PATENT DOCUMENTS

| | | |
|---|---|---|
| EP | 1 475 745 A1 | 11/2004 |
| JP | 04-314181 | 11/1992 |
| JP | 07-085247 | 3/1995 |
| JP | 07-282247 | 10/1995 |
| JP | 2001-309177 | 11/2001 |
| JP | 2002-095635 | 4/2002 |
| JP | 2005-006856 | 1/2005 |
| WO | WO 92/08405 | 5/1992 |

OTHER PUBLICATIONS

Canadian Office Action dated Feb. 29, 2012 from corresponding Canadian Patent Application No. CA 2,602,906.

\* cited by examiner

FIG.6
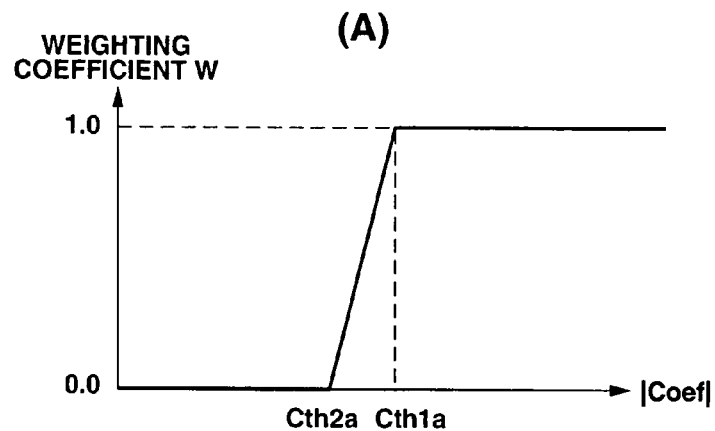
(A)
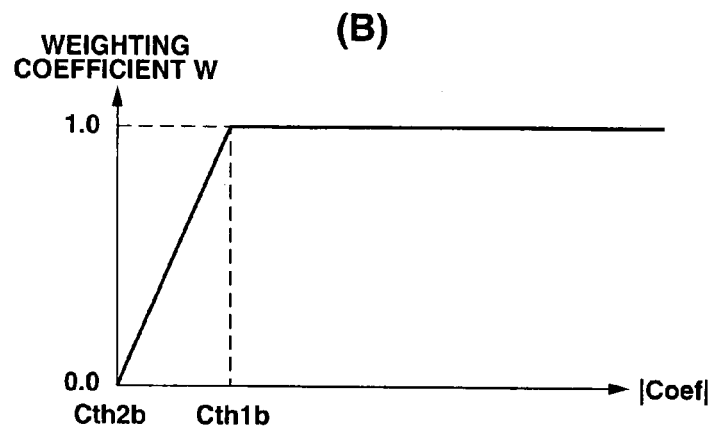
(B)
FIG.7
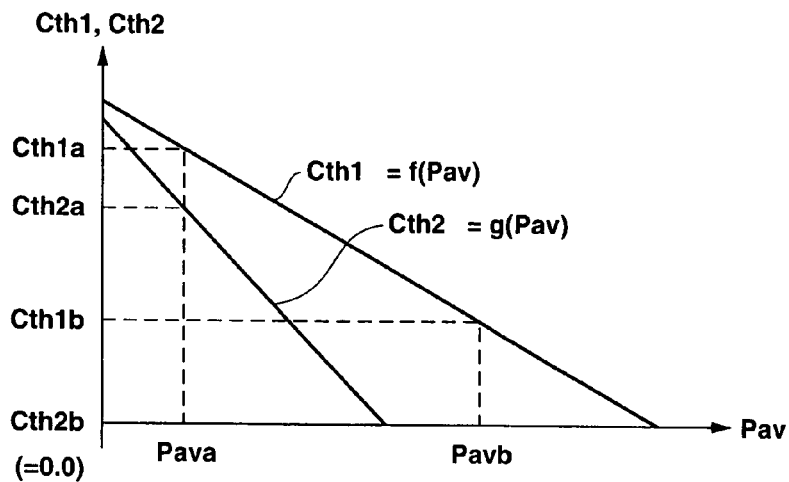

FIG.19
(A)
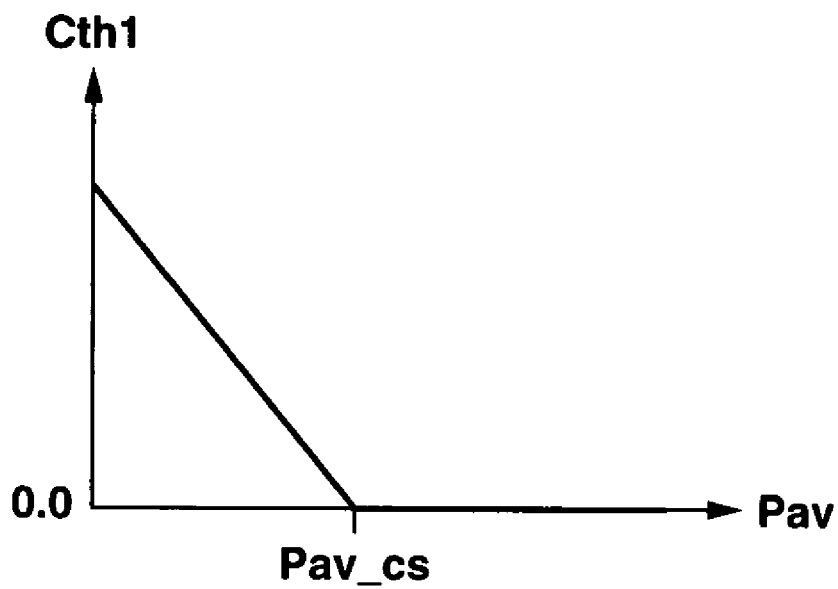
(B)
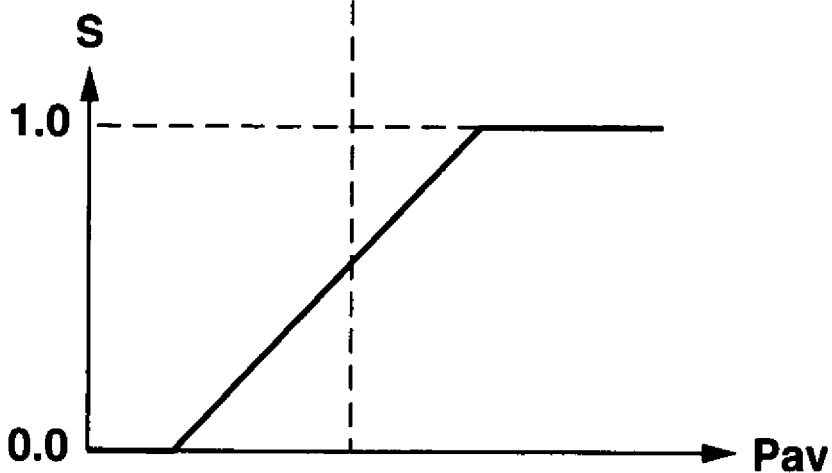

| 100 | 255 | 255 |
|-----|-----|-----|
| 50  | 255 | 255 |
| 80  | 120 | 100 |

FIG.28
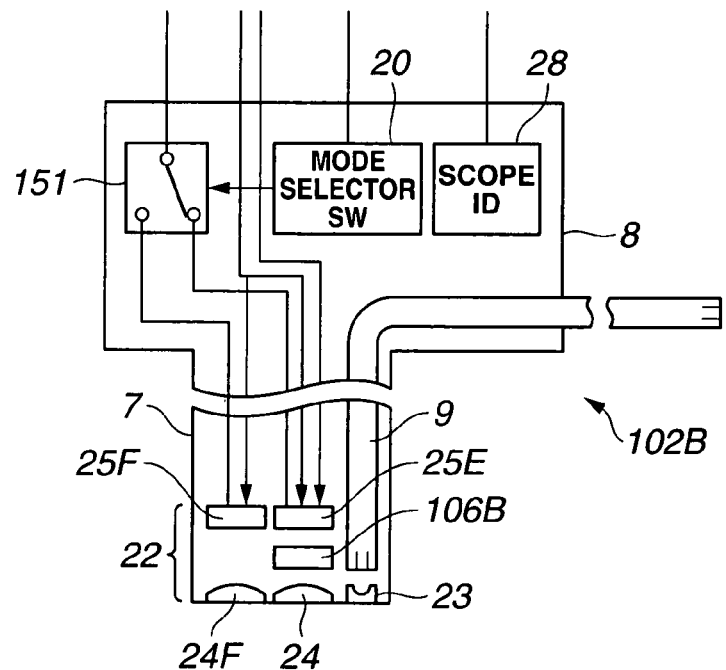
FIG.29
(A)
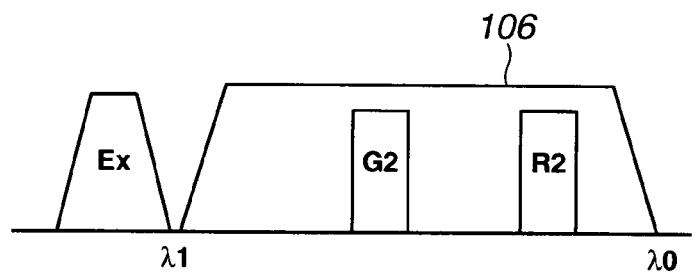
(B)
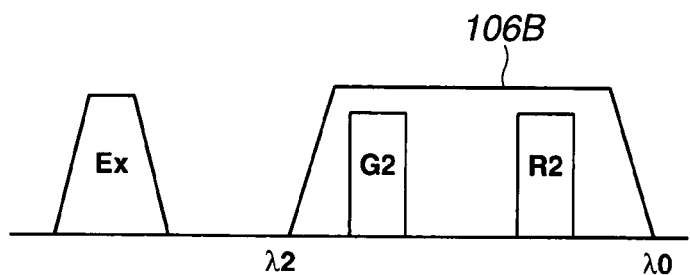

IMAGE PROCESSOR AND ENDOSCOPE APPARATUS

TECHNICAL FIELD

The present invention relates to an image processor and an endoscope apparatus which are suitable for suppressing noise to image data picked up by image pickup means of an endoscope.

BACKGROUND ART

Recently, an electronic endoscope equipped with image pickup means has been widely used not only for conducting a normal observation but also for conducting the special light observation.

For example, Japanese Unexamined Patent Application publication No. 2002-95635 discloses the endoscope apparatus for conducting the special light observation to provide a narrow-band light observation image.

When the narrow-band light observation image is provided, the irradiation light intensity is reduced owing to the narrow-band. If the image information derived from the image pickup device is directly outputted to the monitor, the resultant image may become darker than the image obtained through the normal light observation.

As conventionally employed means for compensating the brightness, a light modulation signal is generated to control the opening/closing degree of the aperture of the light source device so as to adjust the illumination light intensity.

Conventionally, a signal picked up by the AGC circuit is amplified to an appropriate level. When the narrow-band light observation image is obtained, the irradiation light intensity is reduced owing to the narrow-band. Even if the illumination light intensity is maximized by controlling the aperture, there may be the case where the light intensity is still insufficient. In the aforementioned case, the signal has been electrically amplified by the AGC circuit and the like.

The dark image caused by the insufficient light intensity indicates the low S/N state. If the signal is amplified by the AGC circuit to realize the predetermined brightness, the noise becomes easily noticeable.

The method for smoothing in the frequency space has been known to suppress the noise as described above. For example, the image data are orthogonally transformed with Fourier base, which is further subjected to the inverse conversion after applying the low-pass frequency filter function. The similar effect may be realized by the process in the real space. Alternatively, the noise suppression method with a local filter has been well known.

In most of the aforementioned methods, the entire image is subjected to the process uniformly. This may reduce the contrast of the image information except noise, for example, image information with respect to the body tissue.

It is an object of the present invention to provide an image processor and an endoscope apparatus for providing an image suitable for the diagnosis by effectively suppressing the noise while alleviating lowering of the contrast.

DISCLOSURE OF INVENTION

Means for Solving the Problem

The present invention provides an image processor for executing an image processing of image data picked up by image pickup means which includes filter process means for filtering the image data with a plurality of spatial filters, brightness calculation means for calculating a brightness in a local area of the image data, weighting means for weighting an output of the filter process means in accordance with an output of the filter process means and/or an output of the brightness calculation means, and inverse filter process means for executing an inverse filtering with respect to an output of the weighting means to generate process image data.

In the aforementioned configuration, the weighting coefficients with respect to the output of the filter process means and the output through the filter process (filtering) in accordance with the output of the brightness in the local area are changed so as to effectively suppress the noise in the dark image area while avoiding lowering of the contrast in the bright image area.

BRIEF DESCRIPTION OF THE DRAWINGS

FIG. 6 is a view showing a characteristic example of a weighting coefficient to the filter process (filtering) result.

FIG. 7 is a view showing a function example of a threshold value that determines the characteristic of the weighting coefficient to the mean value of the pixel value in a local area.

FIG. 12 is a block diagram showing the configuration of the noise suppression circuit where the weighting coefficient value is changed depending on the CCD type and the like.

FIG. 19 is a view showing the characteristic set examples of the weighting coefficient in the case of the weighted average in a modified example.

FIG. 28 is a view showing a configuration of a second electronic endoscope used for the fifth embodiment.

FIG. 29 is a view schematically showing the transmissivity characteristics of an excited light cut filter respectively used for the first and the second electronic endoscopes.

BEST MODE FOR CARRYING OUT THE INVENTION

Figure 1:
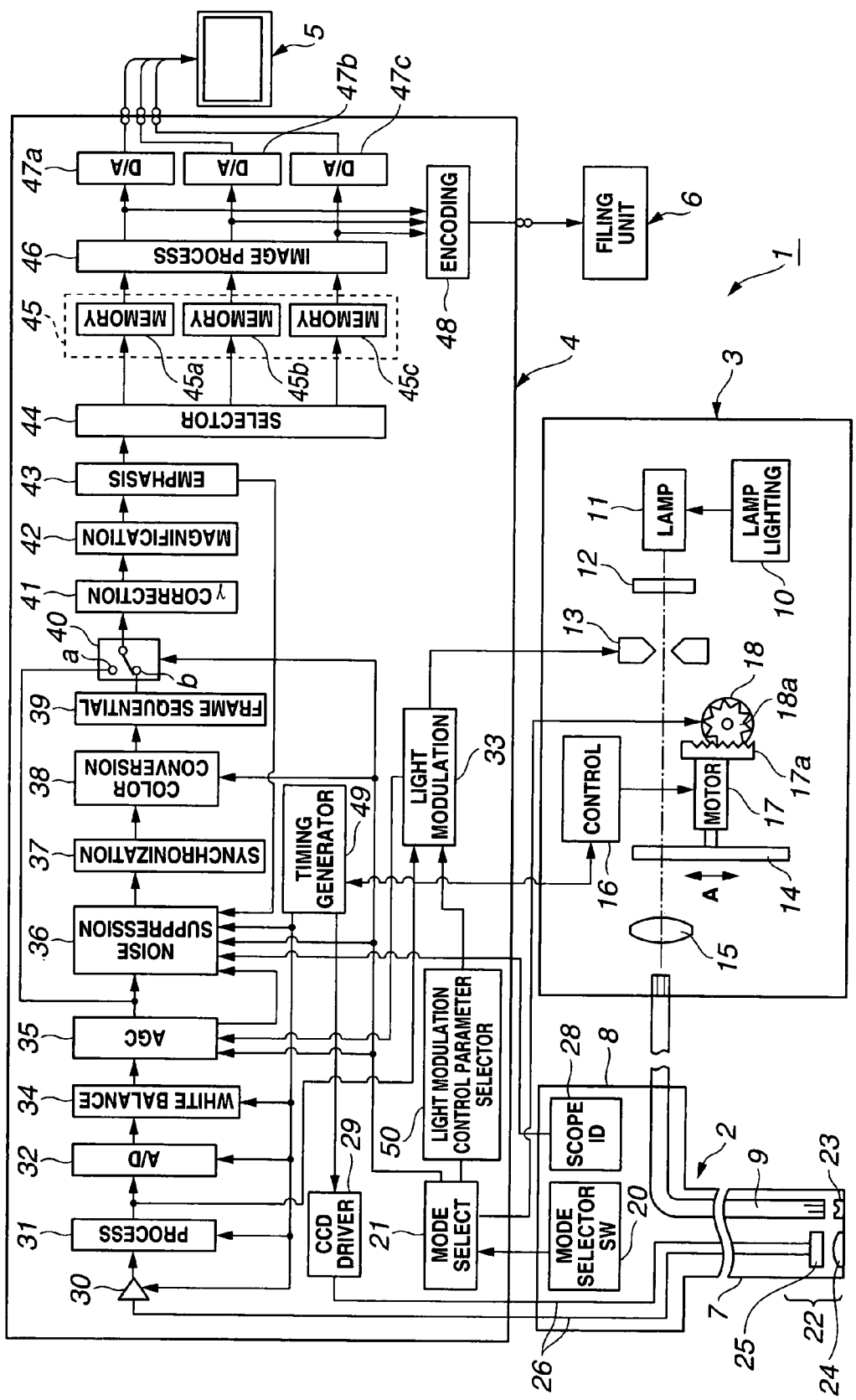
FIG. 1 is a view showing an entire configuration of an endoscope apparatus equipped with a first embodiment of the present invention.

Embodiments of the present invention will be described referring to the drawings.

First Embodiment

Figure 2:
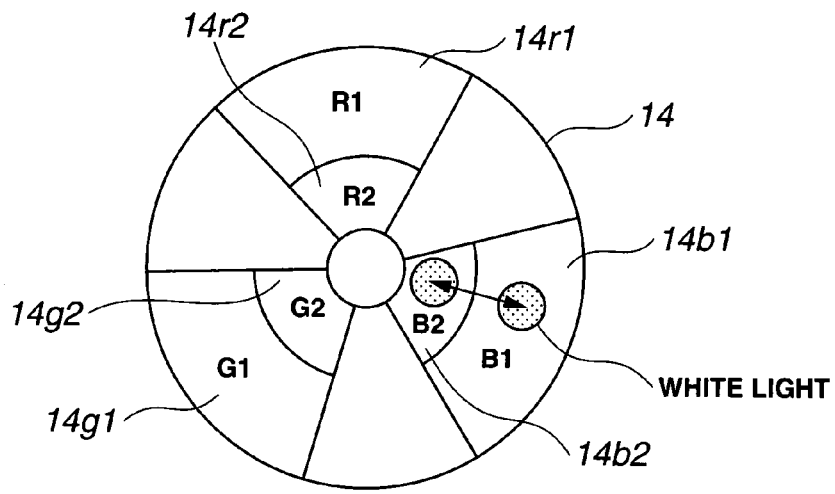
FIG. 2 is a view showing a configuration of a rotary filter shown in FIG. 1.
Figure 3:
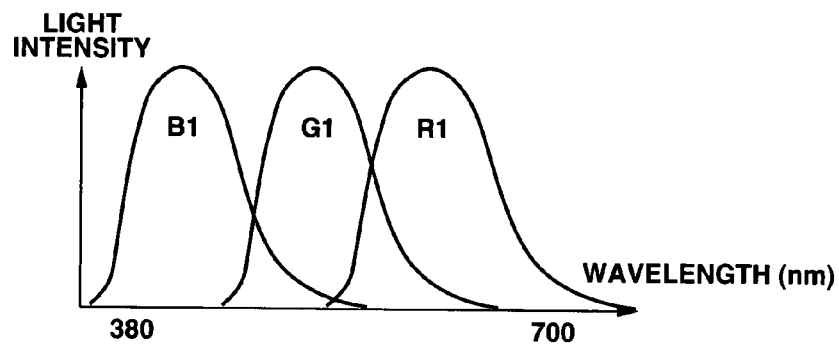
FIG. 3 is a view showing a spectroscopic characteristic of a first filter group of the rotary filter shown in FIG. 2.
Figure 4:
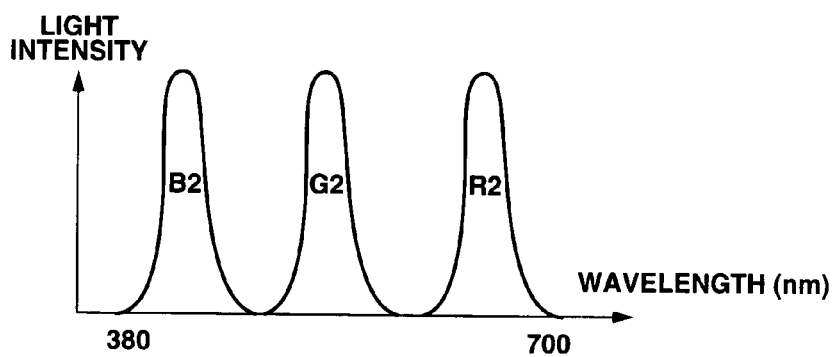
FIG. 4 is a view showing a spectroscopic characteristic of a second filter group of the rotary filter shown in FIG. 2.
Figure 5:
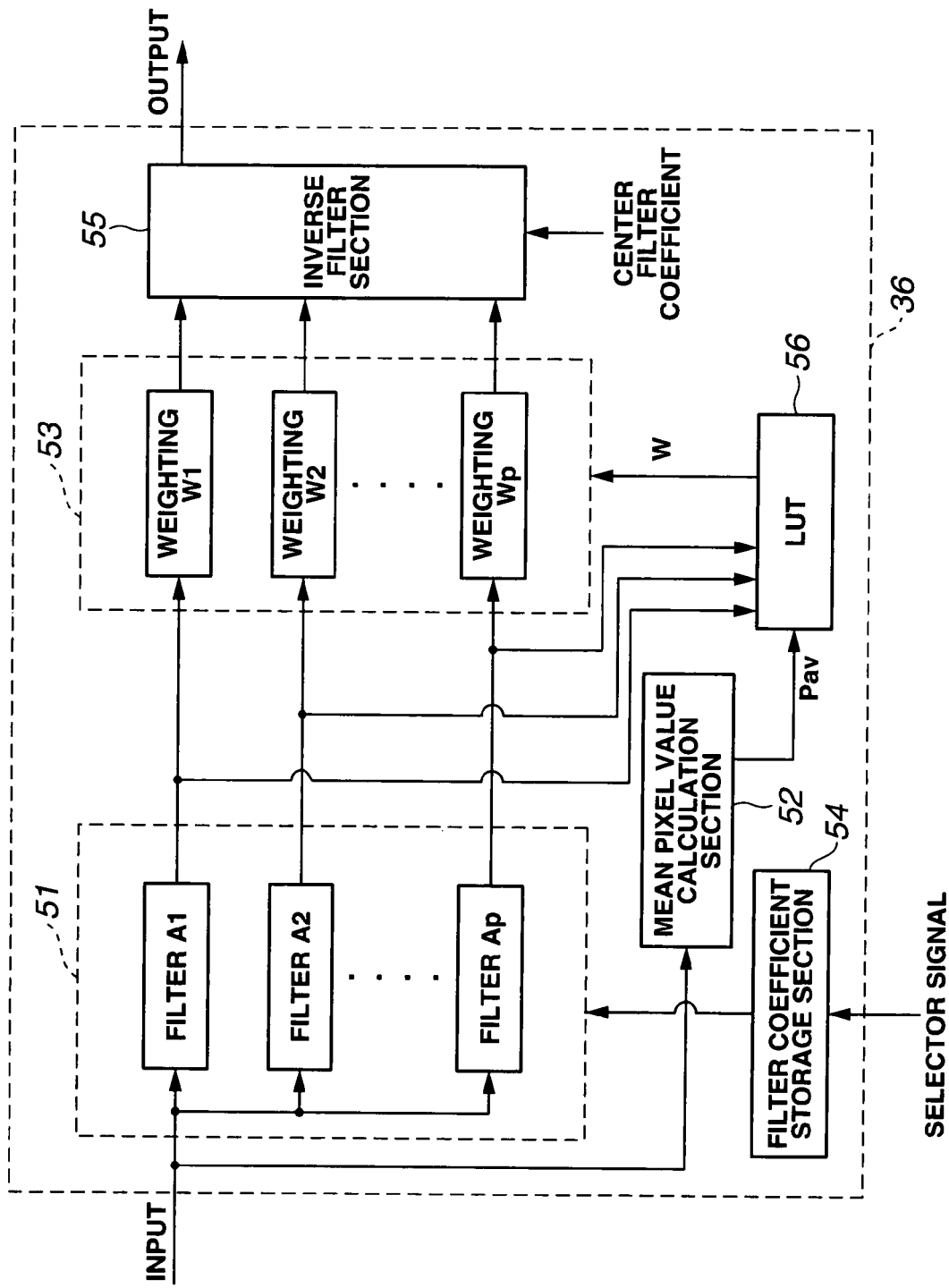
FIG. 5 is a block diagram showing a configuration of a noise suppression circuit.

FIGS. 1 to 10 show the first embodiment of the present invention. FIG. 1 is a view showing an entire configuration of an endoscope apparatus equipped with a first embodiment of the present invention. FIG. 2 is a view showing a configuration of a rotary filter shown in FIG. 1. FIG. 3 is a view showing a spectroscopic characteristic of a first filter group of the rotary filter shown in FIG. 2. FIG. 4 is a view showing a spectroscopic characteristic of a second filter group of the rotary filter shown in FIG. 2. FIG. 5 is a diagram showing a configuration of a noise suppression circuit.

Figure 8:
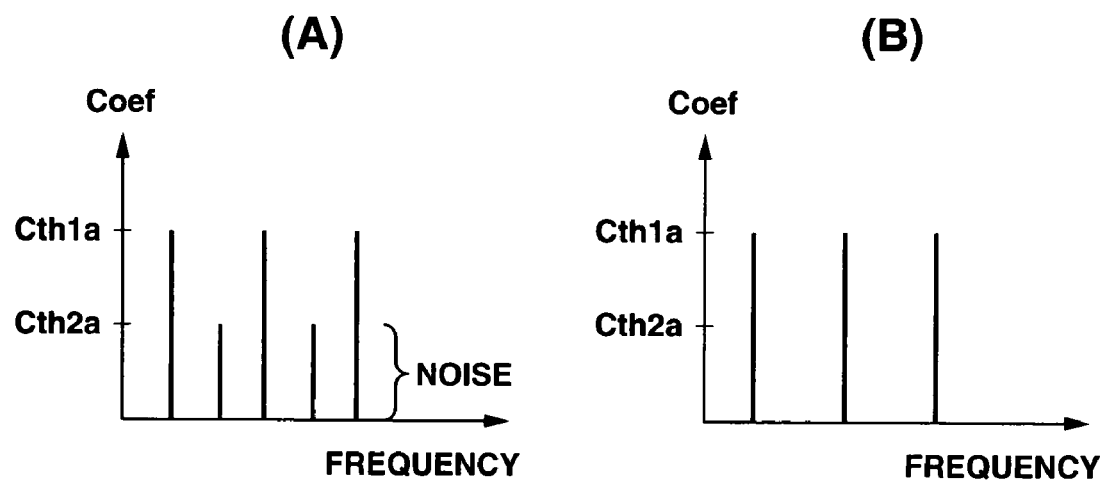
FIG. 8 is an explanatory view of a noise suppressing function in the locally dark portion of the image in the present embodiment.
Figure 9:
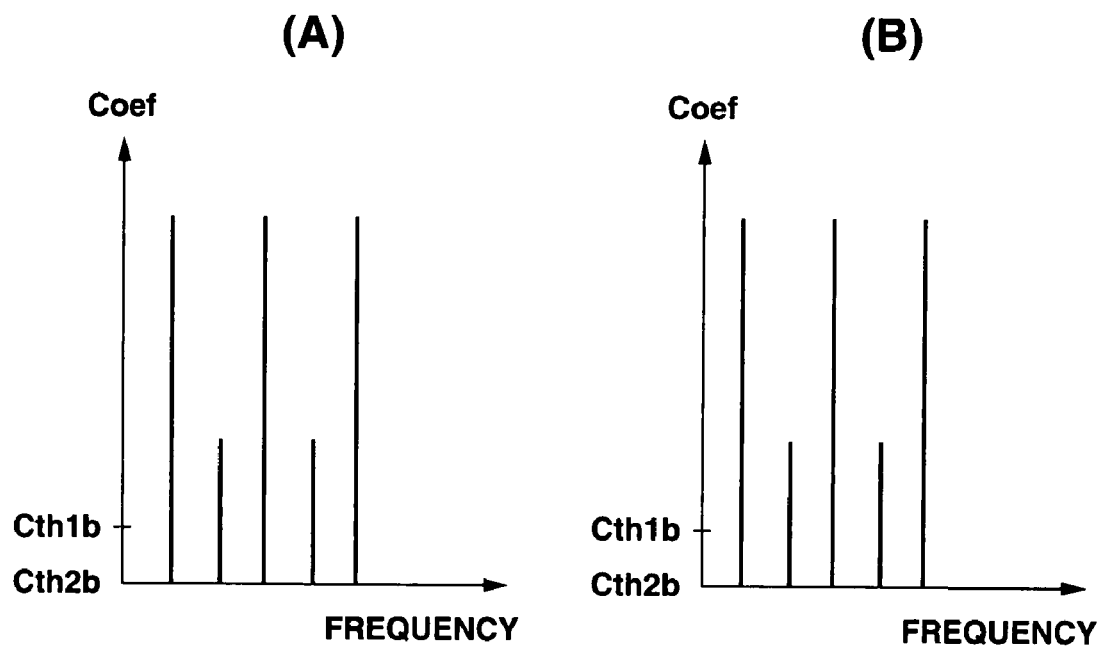
FIG. 9 is an explanatory view of a noise suppressing function in the locally bright portion of the image in the present embodiment.
Figure 10:
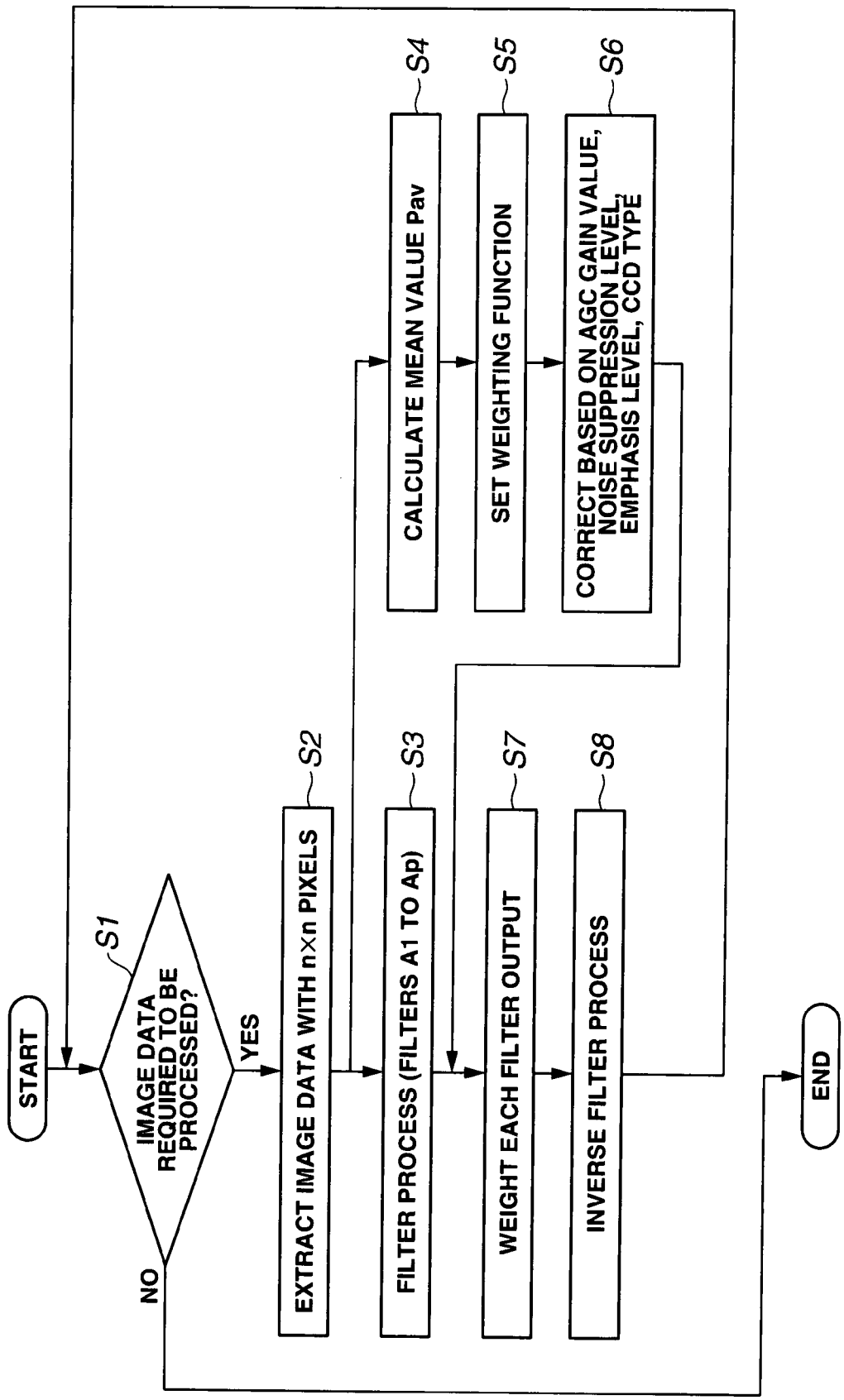
FIG. 10 is a flowchart showing a routine executed in the present embodiment.

FIG. 6 is a view showing a characteristic example of a weighting coefficient to the filter process result. FIG. 7 is a view showing a function example of a threshold value that determines the characteristic of the weighting coefficient to the mean value of the pixel value in the local area. FIG. 8 is an explanatory view of a noise suppressing function in the present embodiment. FIG. 9 is an explanatory view of a noise suppressing function in the present embodiment. FIG. 10 is a flowchart showing a routine executed in the present embodiment.

It is an object of the present embodiment to provide an image processor and an endoscope apparatus equipped with noise suppression process means which suppresses noise in the dark image area and allows the high speed process while alleviating lowering of the contrast in the locally bright image area. It is another object of the present embodiment to provide the endoscopic image processor and the endoscope apparatus for sufficiently suppressing the noise even in the case where the plural types of electronic endoscopes each having different characteristic of the image pickup device are connected.

Referring to FIG. 1, an endoscope apparatus 1 which is equipped with the present embodiment is formed of en electronic endoscope 2 inserted into a body cavity for picking up a body cavity tissue, a light source device 3 for supplying the illumination light to the electronic endoscope 2, a video processor 4 for driving the image pickup means contained in the electronic endoscope 2 to subject the image pickup signal to a signal process, an observation monitor 5 for displaying an endoscopic image generated by the video processor 4, and a filing unit 6 for filing encoded endoscopic images.

The electronic endoscope 2 includes an insertion portion 7 to be inserted into the body cavity. An operation portion 8 is attached to a rear end portion of the insertion portion 7. A light guide 9 is inserted into the insertion portion 7 having its rear end detachably connected to the light source device 3.

The light source device 3 includes a lamp for generating illumination light upon supply of lighting power from a lamp lighting circuit 10, for example, a xenon lamp 11, a hot wire cut filter 12 for blocking the white light heat rays, an aperture unit 13 for controlling a light intensity of the white light via the hot wire cut filter 12, a rotary filter 14 for converting the illuminating light into a frame sequential light, a condenser lens 15 for condensing the frame sequential light via the rotary filter 14 on an incident surface of the light guide 9 disposed in the electronic endoscope 2, and a control circuit 16 for controlling the rotating operation of the rotary filter 14.

The cylindrically formed rotary filter 14 as shown in FIG. 2 has a double configuration with the rotating axis as the center. A circumferential portion with a larger diameter is provided with a first filter group, that is, R1 filter 14r1, G1 filter 14g1 and B1 filter 14b1 for outputting the frame sequential light with overlapped (broader band compared with that of the second filter group) spectroscopic characteristic suitable for the color reproduction as shown in FIG. 3.

The inner circumferential portion is provided with a second filter group including an R2 filter 14r2, a G2 filter 14g2, and a B2 filter 14b2 for outputting the narrow-band frame sequential light with discrete spectroscopic characteristic which allows extraction of the desired deep layer tissue information as shown in FIG. 4.

The rotary filter 14 is controlled to be rotated at a desired speed by the control circuit 16 for driving a rotary filter motor 17 to be rotated as shown in FIG. 1. The rotary filter 14 is moved together with the rotary filter motor 17 by a movement motor 18 in the direction orthogonal to the optical path as shown in the arrow A.

For example, a rack disposed on a holding plate 17a for holding the rotary filter motor 17 is in mesh with a pinion gear 18a disposed on the rotary shaft of the movement motor 18. The movement motor 18 is rotated in the forward or reverse direction in accordance with the drive signal outputted from a mode selector circuit 21 depending on a mode selection command signal of a mode selector switch 20 operated by the user such that the first or the second filter group may be disposed on the optical path in accordance with the observation mode.

In the case where the first filter group is disposed on the optical path, a normal mode is set where the normal frame sequential light is provided such that the normal optical observation image is derived. Meanwhile, in the case where the second filter group is disposed on the optical path, the narrow-band mode (NBI mode) is set where the narrow-band frame sequential light is provided such that the narrow-band light observation image is derived. FIG. 2 shows the position of the light flux obtained in the case where the first and the second filter groups are disposed on the optical path.

The illumination light which has transmitted the first filter group (corresponding to the normal mode) or the second filter group (corresponding to NBI mode) disposed on the optical path, and condensed by the condenser lens 15 is transmitted by the light guide 9 to be irradiated to the tissue in the body cavity through the illumination lens 23 attached to an illumination window of a distal end portion 22 of the insertion portion 7.

An observation window adjacent to the illumination window is provided with an objective lens 24, having a charge-coupled device (hereinafter referred to as a CCD) 25 as an image pickup device on an image-forming position. The CCD 25 conducts the photoelectric conversion of the image-formed optical image.

The CCD 25 is connected to a CCD driver 29 in the video processor 4 and a preamplifier 30 via a signal line 26. The signal line 26 is detachably connected to the video processor 4 via a not shown connector.

The image pickup signal which has been photoelectric converted by the CCD 25 through application of the CCD drive signal from the CCD driver 29 is amplified in the preamplifier 30, and inputted to an A/D conversion circuit 32 via a process circuit 31 for conducting the correlation double sampling and noise elimination as well as to a light modulation circuit 33.

The analog signal is converted by the A/D conversion circuit 32 into the digital signal as the image data, and then further inputted to a white balance circuit 34 where a white balance process is executed. The signal is then inputted to an auto gain control circuit (hereinafter abbreviated to AGC circuit) 35 so as to be amplified to a predetermined level.

The AGC circuit 35 executes the light modulation operation by the aperture unit 13 of the light source device 3 with the illumination light intensity preferentially. After the opening of the aperture unit 13 reaches a release state, the amplification is performed to increase the signal level expected to be insufficient by the AGC circuit 35 based on the release state information.

The light modulation circuit 33 generates a light modulation signal for adjusting an opening degree of the aperture unit 13 of the light source device 3 based on the output signal of the process circuit 31 so as to be controlled to an appropriate illumination light intensity.

The output data of the AGC circuit 35 is inputted to the noise suppression circuit 36, and a γ correction circuit 41 via a selector switch 40.

The selector switch 40 is operated through the mode selector switch 20 to select a contact a in the normal mode, and to select a contact b in the NBI mode via a mode selector circuit 21. In the present embodiment, the side of the noise suppression circuit 36 (from the noise suppression circuit 36 to the frame sequential circuit 39) is activates when the NBI mode is selected.

The noise suppression circuit 36 obtains the image pickup information in the state where the timing signal is transmitted from the timing generator 49, and the second filter group of the rotary filter 14 is disposed on the optical path. The noise suppression circuit 36 selects various parameters for noise suppression by the respective image data of R, G and B from the second filter group (as the color content image of R2, G2 and B2 respectively picked up under the illumination of the R2, G2 and B2) with the second filter group using the timing signal.

The output data of the noise suppression circuit 36 are inputted to a synchronizing circuit 37 where the synchronization is performed, and further to a color conversion circuit 38 where the color conversion is performed. The color conversion circuit 38 subjects the synchronized RGB image information to the color conversion with 3×3 matrix. This makes it possible to improve visibility of the image information reproduced in the NBI mode.

The formula for conducting the color conversion from RGB into R' B' B' uses 3×3 matrix as follows.

$$\begin{pmatrix} R' \\ G' \\ B' \end{pmatrix} = K * \begin{pmatrix} R \\ G \\ B \end{pmatrix} = \begin{pmatrix} 0 & k1 & 0 \\ 0 & 0 & k2 \\ 0 & 0 & k3 \end{pmatrix} * \begin{pmatrix} R \\ G \\ B \end{pmatrix} \quad \text{[Formula 1]}$$

The term K is formed of, for example, three actual numbers components k1 to k3 (other component is zero), and the conversion formula shown above makes the weighting (ratio) of the color signal for the color signal B among those of RGB maximum. In other words, the RGB color image is displayed by suppressing the color signal of R imaged with the transmission light of the R2 filter as the longest wavelength, and emphasizing the color signal of B as the shorter wavelength.

In the above formula (1), the color signal R is completely suppressed. However, the color conversion may be conducted while partially remaining the R color signal component. In the case where the R color signal is completely suppressed as in the formula (1), the R2 is not used as the illumination light as described in the third embodiment. The illumination light of G2 and B2 may only be used.

The output signals (actually, R', G', and B' are set but R, Q and B will be used for the explanation herein) of the color conversion circuit 38 are inputted to the frame sequential circuit 39. The frame sequential circuit 39 formed of the frame memory sequentially reads the simultaneously stored R, G and B image data as the color component image so as to be converted into the frame sequential image data. The frame sequential image data R, G and B are inputted to the γ correction circuit 41 via the selector switch 40 where the γ correction is performed, and thereafter, inputted to a magnification circuit 42 where a magnification interpolation is conducted. The resultant data are inputted to an emphasis circuit 43.

After the structure emphasis or outline emphasis is executed in the emphasis circuit 43, the images are then inputted to a synchronization circuit 45 via a selector 44. The synchronization circuit 45 is formed of three memories 45a, 45b and 45c.

The signal data synchronized in the synchronization circuit 45 are inputted to an image process circuit 46 where the image process such as color shift correction with respect to the video is executed, and then inputted to D/A conversion circuits 47a, 47b and 47c, and encoding circuit 48. The D/A conversion circuits 47a, 47b and 47c convert the data into analogue video signal so as to be inputted to the observation monitor 5.

The observation monitor 5 displays the endoscopic image corresponding to the inputted video signal. The endoscopic image signal compressed in the encoding circuit 48 is inputted to the filing unit 6 so as to be recorded. A timing generator 49 is installed in the video processor 4, to which the synchronizing signal from the control circuit 16 of the light source device 3 in synchronization with the rotation of the rotary filter 14 is inputted. Various timing signals synchronized with the synchronization signal are outputted to the respective circuits.

A scope ID generation circuit 28 is disposed in the electronic endoscope 2 for generating unique information (hereinafter abbreviated to scope ID) for the endoscope identification with respect to the respective endoscopes 2. In the present invention, the information about the CCD 25 of the scope ID is used for the signal process.

In other words, the scope ID is inputted to the noise suppression circuit 36 to allow the noise suppressing process in accordance with the type of the actually used CCD 25. The process for changing the weighting coefficient of the noise suppression circuit 36 in accordance with the type of CCD 25 and the AGC gain value of the AGC circuit 35 and the like will be described in the second embodiment.

The electronic endoscope 2 is provided with the mode selector switch 20 for commanding the mode selection. An output of the mode selector switch 20 is sent to the mode selector circuit 21 in the video processor 4.

The mode selector circuit 21 outputs the control signal in accordance with the command signal for mode selection to a light modulation control parameter selector circuit 50 and the movement motor 18 of the light source device 3, and controls selection of the selector switch 40. The selector switch 40 is operated to select the contact a in the normal mode, and to select the contact b in the narrow-band observation mode (hereinafter abbreviated to NBI mode). The light modulation control parameter selector circuit 50 outputs the light modulation control parameter in accordance with the first or the second filter group of the rotary filter 14 to the light modulation circuit 33. The light modulation circuit 33 controls the aperture unit 13 of the light source device 3 based on the control signal from the mode selector circuit 21 and the light modulation control parameter from the light modulation control parameter selector circuit 50 to execute the appropriate brightness control.

FIG. 5 shows the inner structure of the noise suppression circuit 36. The noise suppression circuit 36 receives inputs of the frame sequential image data of R, G and B as the input image data. The inputted image data are recorded in a not shown memory, and read as image data of n×n pixel while shifting the center pixel by one pixel from the upper left to the lower right. They are inputted to a plurality of filters A1, A2, . . . , Ax, . . . , Ap which form the filter unit 51, and to a mean pixel value calculation section 52 for calculating the brightness in the small area.

The filter unit 51 is formed of p (=n×n) filters each having a filter size of n×n where n denotes the odd number, for example, 3×3, 5×5, and the like. Each of the filters Ax (x=1, 2, . . . , p) serves to execute the convolution with the input image data, and outputs the respective filter process results to a weighting section 53 and a LUT 56.

The coefficients of p filters Ax in the filter unit 51 are selected in accordance with the timing signal (specifically, the selector signal) from the timing generator 49 by the image data of R, G and B, and are read from the filter coefficient storage unit 54 so as to be set.

The coefficient of the filter Ax is derived from the eigenvector of the covariance matrix in the sample data by R, G and B preliminarily formed from the endoscopic images of the sample (specifically, the endoscopic image picked up in the NBI mode).

In the aforementioned case, the eigenvectors are characterized to be orthogonal with each other, and to have Karhunen-Loeve transform (abbreviated to KL transform) matrix. As the eigenvector and the eigenvalue are paired, the eigenvector paired with the larger eigenvalue provides the frequency component corresponding to the lower frequency by conducting the orthogonal transformation with the eigenvector.

In the present embodiment, p-dimensional p eigenvectors are stored in the filter coefficient storage unit 54 in the order of the larger eigenvalue as the filter A1, A2, . . . , Ap. In this case, the filters A1, A2, . . . Ap are arrayed by rearranging in the higher order from the filter coefficients each giving the conversion coefficient corresponding to the lower frequency component.

The filter unit 51 conducts the filter process for the orthogonal transformation with respect to the input image data with p filter coefficients, and outputs the filter process results (orthogonal transmission coefficient) to the weighting section 53.

The mean pixel value calculation section 52 calculates the mean value of the pixel values of n×n pixels in the same input image data for the filter process in the filter unit 51, and outputs the calculation result to the LUT 56.

The weighting section 53 is formed of p (=n×n) weighting circuits W1, W2, . . . , Wp (FIG. 5 shows the weighting W1, W2, . . . , Wp), and the filter process results with respect to the respective filters Ax are inputted to the weighting circuit Wx.

The weighting circuit 53Wx executes the weighting with respect to the filter process results outputted from the filter Ax. The p (=n×n) process results which have been weighted in the weighting circuit 53Wx are outputted to the inverse filter section 55.

The weighting coefficient W for weighting in the weighting circuit 53Wx of the weighting section 53 is preliminarily stored in the LUT 56. The weighting coefficient W corresponding to the mean pixel value calculated in the mean pixel value calculation section 52 and the output of the filter Ax is read from the LUT 56 so as to be set in the weighting circuit 53Wx. The weighting is conducted using the thus set weighting coefficient W.

The inverse filter section 55 generates the image data with noise suppressed by subjecting the inverse filter process (inverse filtering) to the output of the weighting section 53. The generated image data have the values of the pixel as the center of the input n×n pixel data.

In the weighting section 53 of the present embodiment, the value of the weighting coefficient W determined by characteristics as shown in FIG. 6(A) or 6(B) is multiplied by the filter process result Coef using the absolute value of the filter process result in the filter section 51, that is, |Coef| as the variable.

The characteristics of the weighting function as shown in FIG. 6(A) or 6(B) may be determined by two parameters Cth1 and Cth2. More specifically, the parameter Cth1 is a threshold value which allows the weighting coefficient W to be set to 1, and the other parameter Cth2 is a threshold value which allows the weighting coefficient W to be set to 0.

The parameters (threshold values) Cth1$a$ and Cth2$a$, and Cth1$b$ and Cth2$b$ which determine the characteristics shown in FIGS. 6(A) and 6(B) represent the locally dark area and locally bright area of the image, respectively.

Those parameters Cth1$a$, Cth2$a$ and Cth1$b$, Cth2$b$ are determined by a calculated value of the mean pixel value calculation section 52, that is, the mean value Pav of the pixel values in the n×n pixels.

The parameters Cth1$a$, Cth2$a$ and Cth1$b$, Cth2$b$ shown in FIGS. 6(A) and 6(B) are determined in accordance with the Pav$a$ obtained when the mean value Pav is small and with the Pav$b$ obtained when the mean value Pav is large as shown in FIG. 7, respectively.

In the case where the output of the filter process result is larger than the parameter Cth1 as a first predetermined value, the weighting section 53 sets the first predetermined weighting coefficient (specifically, the value 1) irrespective of the output of the filter Ax. Meanwhile, in the case where the output of the filter process result is smaller than the first predetermined value, the weighting coefficient is changed to the smaller value in accordance with the output of the filter Ax. The first predetermined value is changed in accordance with the output of the brightness calculation means.

Specifically, the parameter Cth1 is changed depending on the output of the mean pixel value calculation section 52 such that when the mean value Pav is small (dark), the parameter Cth1 which sets the first predetermined weighting coefficient (specifically the value 1) is changed to the large value, and when the mean value Pav is large (bright), the parameter Cth1 is changed to the small value.

In the present embodiment, the parameter Cth2 as the second predetermined value is changed depending on the output of the mean pixel value calculation section 52. The parameter Cth2 is the value to set the weighting coefficient to 0 in reference to the output of the filter process result to the level for effectively eliminating the noise contained in the output of the filter process result.

The weighting coefficient changes from 0 to 1 between the parameters Cth2 and Cth1.

Based on the weighting function where the Cth1 and Cth2 change with the output of the mean pixel value calculation section 52, the weighting coefficient is set by each filter process result of the filter Ax in accordance with the absolute value |Coef| of the filter process result.

In the case where the mean value Pav is a sufficiently large value as shown in FIG. 7, the relationship of Cth1=Cth2=0.0 is established. Then the value of the weighting coefficient W becomes 1 irrespective of the filter process result. This makes it possible to allow the original image data to be outputted through the inverse filter process to be described later, thus providing the image data with no deterioration in sharpness.

The inverse filter section 55 which subjects the output of the weighting section 53 to the inverse filter process performs the product-sum operation for the product-sum (inner product) of the process results of p outputs from the weighting section 53 to the filter coefficient of the center of the mask (n×n size) of the filter Ax such that the output result after the filter process is returned to the image data of the original observation pixel, that is, the inverse filter process (specifically, inverse KL transform process) is performed.

More specifically, the following formula is established on the assumption that the result of weighting the output of the filter Ax in the weighting circuit Wx is Dx (x=1, 2, . . . , p), and the filter coefficient of the center of the filter Ax is Ax, m (Ax and m denote the mth coefficient of Ax where m denotes an integer obtained by rounding off the value p/2 and p denotes an odd number, that is, (p+1)/2):

$$\Sigma Dx \cdot Ax, m \tag{2}$$

where the code Σ indicating sum which denotes that the products of Dx and Ax, m, that is, Dx·Ax, m are added with the value of the x ranging from 1 to p.

The inverse filter process results through the product-sum operation shown in the formula (2) are outputted to the circuit in the rear stage (synchronization circuit 37) as the pixel values of the results of the process for subjecting the center pixel in the n×n pixel small area in the noise suppression circuit 36.

In the aforementioned embodiment, the weighting coefficient W is determined based on the outputted two parameters Cth1, Cth2, and the filter process result. The weighting function may be determined through two parameters Cth1 and Cth2 with functions f and g having the mean value Pav as the calculated value of the mean pixel value calculation section 52 as the variable as shown in FIG. 7.

In the aforementioned case, both the functions f and g shown in FIG. 7 show characteristics of the monotone decrease, and the slope of the function f is gentler than that of the other function g.

As the functions f and g are set as described above, the weighting functions differ depending on the cases where the Pava has low mean value Pav and the high mean value Pavb of the mean pixel value calculation section 52 as shown in FIGS. 6(A) and 6(B). Accordingly, the weighting coefficient W weighted in the weighting section 53 becomes different.

As the comparison made in FIG. 7 and FIGS. 6(A) and 6(B) shows, if the Pava has the low (small) mean value Pav in the mean pixel value calculation section 52, the weighting coefficient W to the filter process result Coef is set to the small value. On the contrary, if the Pavb has the high mean value Pav in the mean pixel value calculation section 52, the weighting coefficient W to the filter process result Coef is set to the large value.

The weighting coefficient W in the case shown in FIG. 6(A) is set to the value 1 when the filter process result Coef becomes equal to or larger than substantially large threshold value Cth1a. When the filter process result is equal to or smaller than the threshold value Cth2a which is slightly smaller than the Cth1a, the weighting coefficient W is set to 0. In the aforementioned case, the filter process result Coef which is suppressed with the weighting coefficient W is outputted.

The weighting coefficient W in the case shown in FIG. 6(B) is set to the value larger than 0 when the filter process result Coef is larger than 0. When the filter process result is equal to or larger than the substantially smaller threshold value Cth1b, the weighting coefficient W is set to 1. The value of the filter process result Coef is directly outputted.

The noise suppression circuit 36 in the present embodiment adjusts the weighting to the value of the filter process result in the order of brightness of the local area, that is, reduces the weighting as the brightness becomes lower to effectively suppress the noise in the dark image area. The weighting is increased as the brightness becomes higher to maintain the contrast in the image information of the bright image area.

The weighting coefficient W to the filter process result of the filter A1 is always set to 1.0 for the purpose of holding the DC component.

The operation of the above-configured endoscope apparatus according to the present embodiment will be described.

Referring to FIG. 1, the electronic endoscope 2 is connected to the light source device 3 and the video processor 4, and power is supplied to be initially set into a normal observation state, for example.

In the normal observation mode, the mode selector circuit 21 in the video processor 4 controls the movement motor 18 such that the R1 filter 14r1, G1 filter 14g1 and B1 filter 14b1 which form the first filter group of the rotary filter 14 are on the optical path of the illumination light.

In the normal mode for observing the body cavity tissue, wavelength bands of the R1 filter 14r1, G1 filter 14g1 and B1 filter 14b1 overlap with each other as shown in FIG. 3. The image pickup signal of the B1 filter 14b1 picked up by the CCD 25 contains band images of the shallow layer and intermediate layer tissue information containing much tissue information in the shallow layer of the living body tissue. The image pickup signal of the G1 filter 14g1 picked up by the CCD 25 contains band images of the shallow layer and intermediate layer tissue information containing much tissue information in the intermediate layer of the living body tissue. The image pickup signal of the R1 filter 14r1 picked up by the CCD 25 contains band images of the intermediate and deep layer tissue information containing much tissue information in the deep layer.

Those RGB image pickup signals are synchronized to be subjected to the signal process in the video processor 4 to provide the desired endoscopic image or the naturally color reproduced endoscopic image.

In the normal observation mode, the video processor 4 does not subject the image data passing through the AGC circuit 35 to the process in the noise suppression circuit 36, but inputs the image data into the γ correction circuit 41 through the selector switch 40. The image data are subjected to the γ correction process, magnification process and structure emphasis process and the like, and then inputted to the synchronization circuit 45 through the selector 44 where synchronization is executed. Thereafter, the resultant data are subjected to the video color shift correction and the like and converted into the analogue color signal such that the endoscopic image is displayed on the display of the observation monitor 5.

Meanwhile, when the mode selector switch 20 of the electronic endoscope 2 is depressed, the resultant signal is inputted to the mode selector circuit 21 in the video processor 4. The mode selector circuit 21 outputs the control signal to the movement motor 18 in the light source device 3 to move the first filter group of the rotary filter which has been on the optical path in the normal observation mode. Then the rotary filter 14 is moved to set the NBI mode such that the second filter group is disposed on the optical path.

In the NBI mode, the R2 filter 14r2, G2 filter 14g2 and B2 filter 14b2 which form the second filter group have discrete narrow-band spectroscopic characteristics as shown in FIG. 4, which become narrow-band frame sequential light as the rotary filter 14 rotates.

In the aforementioned case, the image pickup signal of the B2 filter 14b2 picked up by the CCD 25 contains the band images including the tissue information in the shallow layer. The image pickup signal of the G2 filter 14g2 picked up by the CCD 25 contains the band images including the tissue information in the intermediate layer. The image pickup signal of the R2 filter 14r2 picked up by the CCD 25 contains the band images including the tissue information in the deep layer.

In this case, referring to FIGS. 3 and 4, as the transmission intensity of the second filter group decreases as its band becomes narrow relative to the transmitted light intensity of the first filter group, the light modulation control parameter selector circuit 50 outputs the light modulation control parameter to the light modulation circuit 33 in accordance with the second filter group of the rotary filter 14 to allow the light modulation circuit 33 to control the aperture unit 13.

In the NBI mode, as the illumination light intensity is reduced to a large degree compared with the normal mode, the aperture unit 13 is mostly set to an open state.

Even if the aperture unit 13 is set to the open state, the illumination light intensity may be in the low state compared with the normal mode. In such a case, the brightness insufficiency owing to the low illumination light intensity may be electrically corrected by amplifying the picked up image. The image resulting from the aforementioned amplification factor by the AGC circuit 35 may have the noise in the dark image portion easily distinguished. In the present embodiment, the image is inputted to the noise suppression circuit 36 as shown in FIG. 5 to alleviate the lowering of the contrast in the bright area while suppressing the noise in the dark area to be described later.

The image data of R, G and B converted into digital signals in the A/D conversion circuit 32 and amplified in the AGC circuit 35 are inputted to a filter section 51 which forms the noise suppression circuit 36 as shown in FIG. 5. The data are inputted to p filters A1, A2, ..., and Ap each having the size n×n for forming the filter section 51 and to the mean pixel value calculation section 52.

The filter section 51 subjects the input image data to the filter process using the filter coefficient based on the KL transform matrix preliminarily derived from the sample image data. The filter process results are outputted to the weighting section 53.

The mean pixel value calculation section 52 calculates the mean value Pav of the pixel values in the small area (local area) with n×n size of the input image data which are the same as those used for the space filter process in the filter section 51. Depending on the resultant mean value Pav and the filter process result value, the weighting coefficients W for the weighting circuits W1, W2, ..., Wp in the weighting section 53 are set through the LUT 56.

In the present embodiment, the weighting coefficient W is determined depending on the absolute value of the filter process result Coef after setting two parameters Cth1 and Cth2 having the characteristics determined based on the mean value Pav shown in FIG. 7. In case of the dark image portion, the weighting coefficient W is set as shown in FIG. 6(A), and in case of the bright image portion, the weighting coefficient W is set as shown in FIG. 6(B) based on the parameters Cth1 and Cth2. The parameters Cth1a and Cth2a are used for the dark image area, and Cth1b and Cth2b are used for the bright image area as shown in FIGS. 6(A) and 6(B).

As the weighting coefficient is set as shown in FIGS. 6(A) and 6(B), when the absolute value of the filter process result Coefx (Coef in FIG. 6) of the filter Ax is small, that is, the portion having the low S/N, the weighting coefficient W is decreased. Meanwhile, when the absolute value of the filter process result Coefx is large, the weighting coefficient is increased.

When the mean value Pav is small, the weighting process in the weighting section 53 changes the input data shown in FIG. 8(A) to the one as the result shown in FIG. 8(B). FIG. 8 shows the respective filter processed frequency components.

Referring to FIG. 8(A), the value of the parameter Cth2 is set to the level of random noise such that the noise is effectively suppressed and the lowering of the frequency component based on the high S/N image information is alleviated, thus providing the results shown in FIG. 8(B). The use of the parameter Cth1 allows high noise suppression effect while avoiding the relative decrease in the high S/N frequency component. Accordingly, this makes it possible to alleviate lowering of the image information contrast with respect to the mucosa in the dark image area.

Meanwhile, when the mean value Pav is large, the parameter Cth2 becomes 0, and another parameter Cth1 is set to the lower value. The filter process result Coef inputted to the weighting section 53 is substantially directly outputted.

When the mean value Pav is large, the input data shown in FIG. 9(A) is subjected to the weighting process in the weighting section 53 to provide the results shown in FIG. 9(B). In this case, as the data inputted to the weighting section 53 are substantially directly outputted, the lowering of the contrast in the bright image area may be avoided.

The output of the result of the weighting process in the respective weighting circuits Wx in the weighting section 53 is inputted to the inverse filter section 55 where the inverse filter process (specifically, the inverse KL transform) is executed by the product-sum operation of the center filter coefficient Ax, m of the respective filters Ax in the filter section 51. The image data with the noise suppressed pixel value is outputted to the synchronization circuit 37 in the next stage.

When the process of the R image data by 1 frame is finished, the image data are stored in the R frame memory in the synchronization circuit 37 by the noise suppression circuit 36. Then the noise suppression circuit 36 starts processing the next G image data by 1 frame. When the process is finished, the processed G image data are stored in the G frame memory in the synchronization circuit 37.

In this case, the timing generator 49 selects the filter coefficient of the filter coefficient storage section 54 in the noise suppression circuit 36 and the weighting coefficient table of the LUT 56 to execute the same filter process with the filter coefficient corresponding to the G image data. When the process of the G image data by 1 frame is finished, the process for the B image data by 1 frame is started. When the process is finished, the processed B image data are stored in the B frame memory in the synchronization circuit 37. In this case, the noise suppression circuit 36 executes the same filter process with the filter coefficient corresponding to the B image data.

The image data of R, G and B stored in the synchronization circuit 37 are simultaneously read, and inputted to the color conversion circuit 38 where the conversion of the displayed color is executed for improving the visibility in case of the color display. The image data of RGB which have been color converted in the color conversion circuit 38 are converted into the frame sequential signal in the frame sequential circuit 39.

The frame sequential signal is inputted to the γ correction circuit 41 via the selector switch 40, and thereafter, the same process as in the normal mode is executed such that the NBI image in the NBI mode is displayed on the observation monitor 5.

The entire control procedure executed in the noise suppression circuit 36 will be shown in FIG. 10. When the noise suppression circuit 36 starts operating, it is determined whether or not the image data required to be processed exist in step S1.

Specifically, any one of the RGB image data are inputted to the noise suppression circuit 36 to extract the image data with n×n pixel from the head to the end of the image sequentially as the image data to be processed while shifting the center pixel one by one. It is determined whether or not the image data with n×n pixel to be extracted exist. If no image data to be extracted exist, the process is terminated. If it is determined that the image data to be extracted exist, the process proceeds to subsequent step S2.

In step S2, the image data with n×n pixel are extracted from the image data to be processed, and in subsequent step S3, the image data with n×n pixel is subjected to the filter process with the filters A1 to Ap in the filter section 51. Then the mean value Pav is calculated in the mean pixel value calculation section 52 as shown in step S4.

When the mean value Pav is calculated, the weighting function is set with respect to the filter output based on the mean value Pav as shown in step S5.

In step S6, the weighting function is corrected based on the AGC gain value, noise suppression level in the noise suppression section (NR level adjusting section), emphasis level in the emphasis circuit 43, and the CCD type to be described in the second embodiment, and then the process proceeds to step S7.

In step S7, the weighting coefficient W corresponding to the filter process result value is obtained in reference to the weighting function, that is, the LUT 56 at every output of the filter process executed in step S3. The weighting coefficient W is multiplied by the filter process result for performing the weighting.

The weighting process makes it possible to effectively suppress the noise particularly in the dark area and to avoid lowering of the contrast in the bright area. The process then proceeds to step S8.

In step S8, the product-sum operation is performed to the weighting process results at the respective frequency components with the predetermined coefficient of the filter Ax to execute the inverse filter process such that the center pixel value of the n×n pixel is obtained. The process then returns to step S1. In step S1, the determination with respect to the presence/absence of the pixel data to be processed is made again. If the pixel data are present, the process further proceeds to subsequent step S2 where the image data with n×n pixel adjacent to the center pixel of the aforementioned n×n pixel are extracted, and thereafter, the similar process will be repeatedly executed.

All the image data to be processed are subjected to the aforementioned process repeatedly. When all the image data are processed, the routine ends.

In the present embodiment, the degree of weighting to the filter process result Coef is changed depending on the local brightness in the image and the value of the filter process result Coef such that the noise which is especially distinguishable in the dark area is suppressed, and the lowering of the image contrast except the noise is alleviated as well as avoiding the lowering of the image contrast in the bright area.

The present embodiment makes it possible to provide the endoscopic image suitable for the diagnosis even if the especially dark image portion exists.

In the present embodiment, the filter coefficient and the weighting coefficient W are selected with respect to each image of R, G and B. However, the present embodiment may be modified by commonly using those coefficients with no need of selection with respect to each image of R, G and B so as to reduce the size of the noise suppression circuit 36.

In the aforementioned explanation, the noise is suppressed by using the KL transform base as the filter coefficient to the sample image data. Alternatively, as another modified example, the discrete cosine transform (DCT) base may be used for executing the filter process common to the respective images of R, G and B.

The use of the DCT allows the filter coefficient to be symmetrical, thus reducing the circuit size as well as the number of operations required for the noise suppression, resulting in the high-speed process.

In the aforementioned explanation, the LUT 56 based on which the weighting coefficient W in the weighting section 53 is set is used common to the filter section 51 entirely. However, the LUT 56 may be individually provided with respect to each output of the filter Ax.

The aforementioned manner increases freedom degree in the weighting to enable the noise suppression effect to be increased while alleviating lowering of the contrast of especially dark image information. For example, there is the noise specific to the image information derived from the endoscopic system, image pickup device, or the narrow-band light except the random noise, the weighting coefficient to the filter process result corresponding to the frequency component is appropriately set so as to effectively suppress the noise. This makes it possible to provide the image suitable for the diagnosis.

Second Embodiment

A second embodiment according to the present invention will be described referring to FIG. 11. The present embodiment is formed by modifying the first embodiment. The present embodiment is intended to effectively suppress noise in the case where the electronic endoscope equipped with different type of image pickup means is connected, or the outline or the structure emphasis level is changed.

In the first embodiment, the noise suppression circuit 36 is commonly used independent from the type of the CCD 25. In the present embodiment, the weighting coefficient is changed in the weighting section depending on the type of the CCD 25, the gain value of the AGC circuit 35 which is set in the operation state (AGC ON), and the emphasis level of the emphasis circuit 43. The other configuration is the same as that of the first embodiment.

Figure 11:
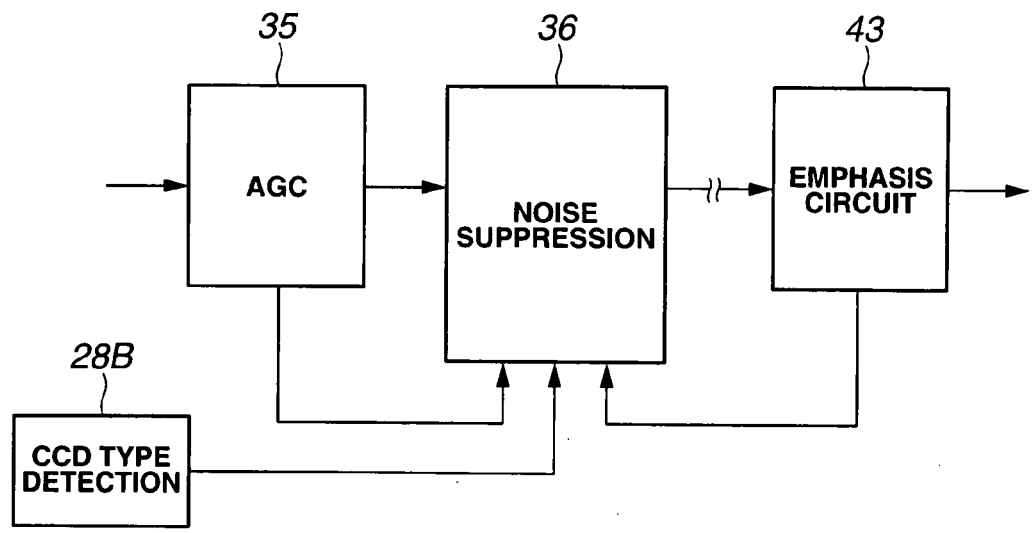
FIG. 11 is a block diagram showing the configuration of a portion around the noise suppression circuit according to a second embodiment of the present invention.

FIG. 11 shows the configuration of the circuit around the noise suppression circuit 36 in the second embodiment. Likewise the first embodiment, in the second embodiment, the output signal of the AGC circuit 35 is inputted to the noise suppression circuit 36 where the noise is suppressed, and is further inputted to the emphasis circuit 43 via the synchronization circuit 37 and the like.

In the present embodiment, the information data in the AGC gain of the AGC circuit 35, the emphasis level of the emphasis circuit 43, and the type of the CCD 25 detected by the CCD type detection circuit 28B in the electronic endoscope 2 are inputted to the noise suppression circuit 36. The CCD type detection in the CCD type detection circuit 28B shown in FIG. 11 may be performed by the scope ID in a scope ID generation circuit 28. Alternatively, the type of the CCD 25 may be detected by a connector pin of a not shown connector detachably connected to the video processor 4.

Figure 12:
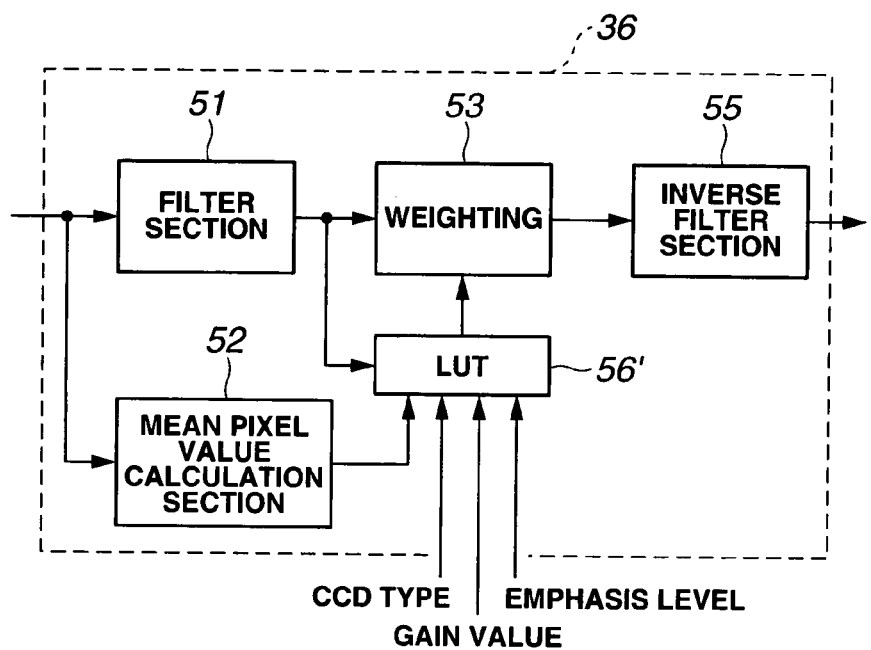

More specifically, the information data including the output of the filter section 51, the mean value (output value) as the output of the mean pixel value calculation section 52, the type of the CCD 25, the AGC gain value of the AGC circuit 35, and the emphasis level of the emphasis circuit 43 are inputted to the LUT 56' in the noise suppression circuit 36 as shown in FIG. 12. Based on the aforementioned information data, the weighting coefficient W in the weighting section 53 is appropriately set (by changing the parameters Cth1 and Cth2).

The noise level of the CCD 25 may differ by the type thereof. The present embodiment is configured to change the weighting coefficient corresponding to the noise level of the CCD 25 which differs by the type.

Specifically, assuming that there are four types of the CCD 25 each having the different noise level, CCD 25A, CCD 25B, CCD 25C and CCD 25D in the order of the low noise level, the corresponding weighting coefficient may be set in accordance with the noise level value. For example, the type of the CCD 25, that is, CCD 25I (I=A to D) is detected, the correction coefficient CI corresponding to the detected type is multiplied by the parameter Cth (Cth is a collective term of Cth1 and Cth2). The relationship of CA<CB<CC<CD is established.

In the aforementioned setting, the small weighting coefficient may be applied to the CCD with the high noise level. This makes it possible to provide appropriate suppression effect irrespective of the CCD type.

In order to prevent fluctuation of the noise suppression effect depending on the gain value of the AGC circuit 25, the weighting coefficient value is corrected in accordance with the gain value.

Specifically, as the gain value increases, the mean value Pav for the brightness becomes apparently large in proportion to the gain value. For this, the functions f(Pav) and g(Pav) shown in FIG. 7 are required to be changed by, for example, increasing the scale of the Pav on the x-axis or Cth on the y-axis by gain times.

Figure 13:
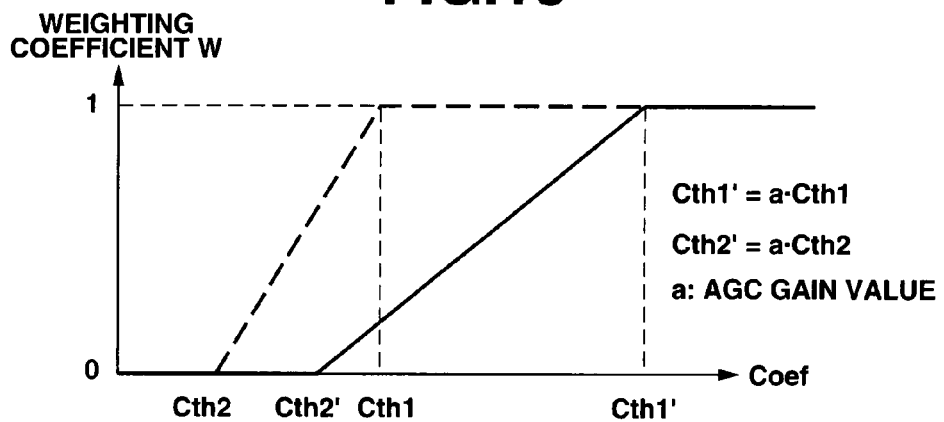
FIG. 13 is an explanatory view showing the change in the weighting coefficient in accordance with the AGC gain value.

In FIG. 13, the dotted line represents the characteristic of the weighting coefficient W set based on the parameters Cth1 and Cth2 when the gain is 1. The solid line represents the characteristic of the weighting coefficient W which is set when the gain value is increased by a times (a=2 in FIG. 13). Values of the parameters Cth1' and Cth2' represented by the solid line establish the following formulae.

$$Cth1'=Cth1\times a$$

$$Cth2'=Cth2\times a$$

The aforementioned correction changes the weighting coefficient W in accordance with the filter process result Coef which varies with the gain. The noise suppression independent from the gain may be performed.

The output portion of the mean pixel value calculation section 52 as the brightness calculation means may be provided with a divider for dividing the output of the mean pixel value calculation section 52 by the gain value. The output portion of the filter Ax may be provided with a divider for dividing the respective filter process results by the gain value. The output portion of the respective weighting circuits Wx may further be provided with a multiplier for multiplying the respective weighting results by the gain value. In the aforementioned cases, the weighting coefficient does not have to be corrected.

In the case where the structure emphasizing is performed in the emphasis circuit 43, the correction coefficient Cj corresponding to the emphasis level is multiplied by the parameter Cth such that the value of the weighting coefficient W becomes small as the emphasis degree is increased.

When the structure emphasis is intensified in the aforementioned way, the noise becomes noticeable in general. However, the present embodiment allows the noise to be less noticeable in the dark image area.

Upon execution of the structure emphasis, when the specific frequency component is emphasized, the value of the weighting coefficient W to the filter output result corresponding to the frequency may be decreased.

Other configuration is substantially the same as that of the first embodiment.

The above-configured embodiment provides the same effects as those derived from the first embodiment, and allows the appropriate noise suppression even if the type of the CCD 25, the gain value of the AGC circuit 35, and the emphasis level of the emphasis circuit 43 are changed.

In response to change in the type of the CCD 25, the noise which is likely to be noticeable especially in the dark image area may be effectively suppressed and lowering of the contrast in the image portion except the noise may be alleviated so as to provide the image suitable for the diagnosis.

As a first modified example of the present embodiment, an NR level adjustment section for adjusting the noise suppression level (abbreviated to the NR level) is provided on the front panel in the video processor 4, for example. The weighting coefficient in the weighting section 53 may be changed in accordance with the change in the NR level by operating a knob (or a switch) for variably setting the NR level in the NR level adjustment section.

Figure 14:
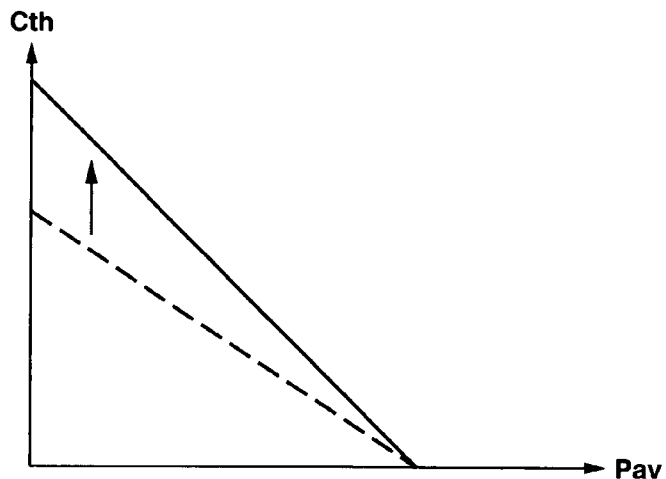
FIG. 14 is an explanatory view showing the change in the parameter characteristic which determines the weighting coefficient depending on the change in the noise suppression level.

Specifically, if the knob is operated to change the low NR level to the high NR level, the parameter Cth (that is, Cth1 and Cth2) which determines the weighting coefficient W of the weighting section 53 is shifted from the characteristic as shown by the dotted line to the one as shown by the solid line in FIG. 14. FIG. 14 uses the Cth as the collective term of the aforementioned parameters Cth1 and Cth2.

Referring to FIG. 14, the value of the parameter Cth is increased relative to the mean value Pav of the brightness. For example, the correction coefficient corresponding to the NR level is multiplied by the Cth value.

In the case where the low NR level is changed to the high NR level, the value of the weighting coefficient W to the filter process result Coef is set to the small value according to the change, thus improving the noise suppressing function.

In the case where the NR level is changed, the position which crosses the x-axis is kept unchanged as shown in FIG. 14 so as not to change the brightness of the image on which the noise suppression function starts working.

The user is allowed to freely set the noise suppression effect by changing the NR level to satisfy the user's requirement, for example to the state where the image quality considered as being appropriate by the user is obtained without changing the brightness of the image on which the noise suppression function starts working.

In the first modified example, the brightness at which the noise suppression function starts working is not changed. In the second modified example, the brightness may be changed in conjunction with the change in the NR level.

Figure 15:
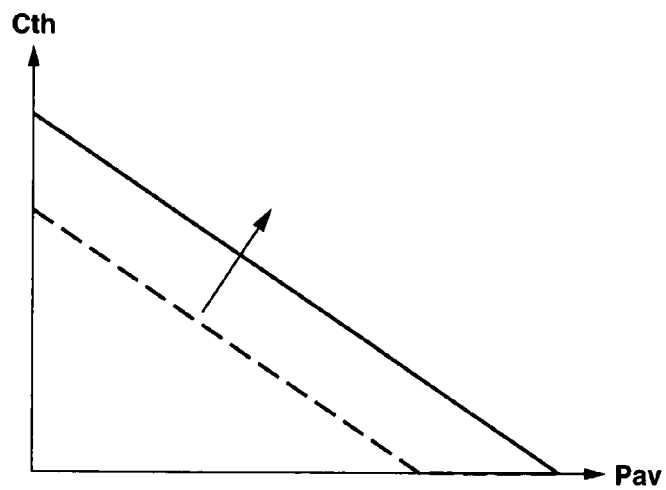
FIG. 15 is an explanatory view showing the characteristic which is different from the one shown in FIG. 14.

In the second modified example, in the case where the low NR level is changed to the high NR level, the parameter Cth is changed from the characteristic indicated by the dotted line to the one shown by the solid line as shown in FIG. 15 accompanied with the change in the NR level.

In the characteristic view for determining the parameter Cth with respect to the mean value Pav, each section value of the Pav axis and Cth axis is changed with the correction coefficient corresponding to the NR level. When the NR level is increased, the values of both sections are simultaneously increased.

This makes it possible to change the brightness at which the noise suppression effect starts working, and the noise suppression effect to the brightness to satisfy the user's requirement.

A plurality of characteristics as shown in FIG. 15 are provided to select the value therefrom.

In the present embodiment, the weighting coefficient is changed based on the gain of the AGC circuit, the type of the CCD 25, the emphasis level and the NR level. The weighting coefficient may be changed based on at least one of the aforementioned values.

In the case where the weighting coefficient is changed based on the gain of the AGC circuit 35, the gain can be replaced with the gain of the amplifier which amplifies the input signal to the noise suppression circuit 36.

Third Embodiment

A third embodiment of the present invention will be described referring to FIGS. 16 to 19. The present embodiment is intended to improve the noise suppressing function while suppressing the circuit size.

In the present embodiment, the weighted mean is performed with respect to the output of the inverse filter process and the original pixel value using the output value of brightness in the first or the second embodiment.

Figure 16:
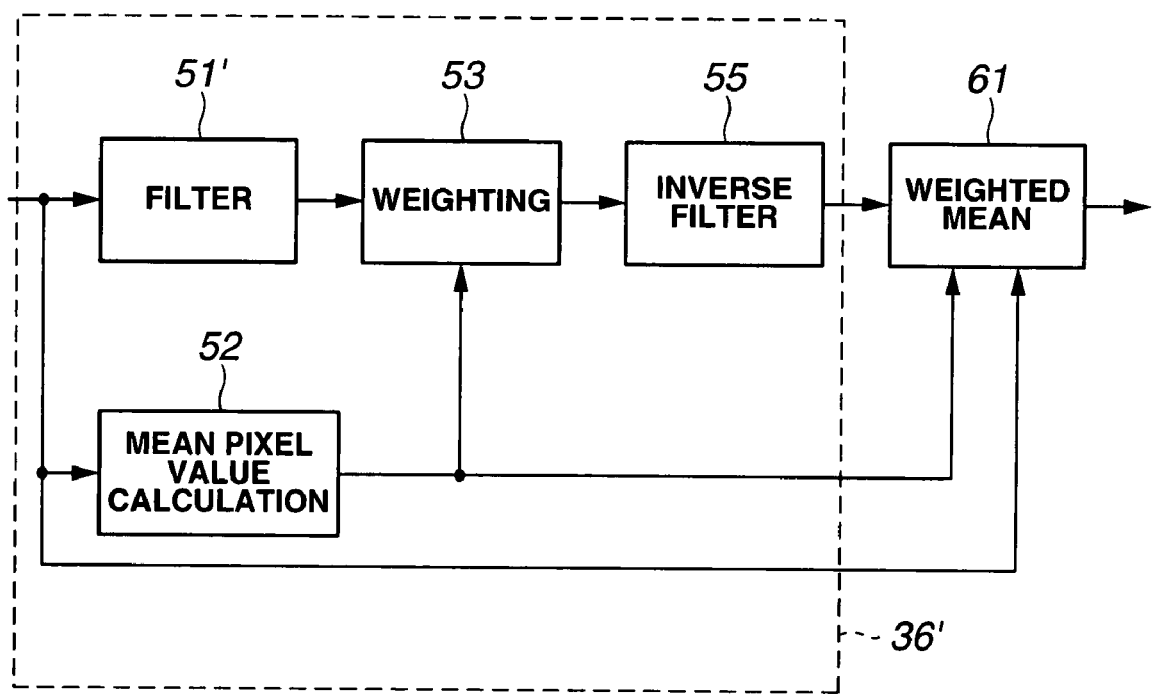
FIG. 16 is a block diagram showing a configuration of a portion around a noise suppression circuit according to a third embodiment of the present invention.
Figure 17:
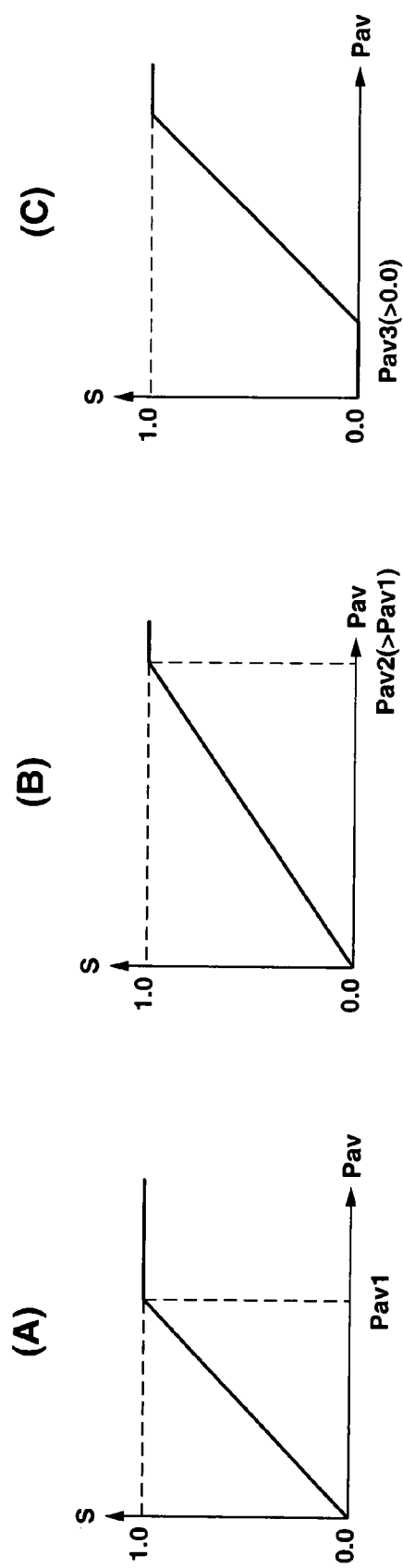
FIG. 17 is a view showing the characteristic set examples of the weighting coefficient for weighted average with respect to the mean value of brightness in a weighted average section.

FIG. 16 shows the configuration of the circuit around the noise suppression circuit in the third embodiment. The present embodiment employs a noise suppression circuit 36' including a filter section 51' with the larger filter size than that of the filter section 51 in the noise suppression circuit 36 in the first embodiment.

When the filter size is increased to make the frequency resolution high, the noise suppression effect may be improved, but the circuit size is increased.

For the purpose of providing the pixel value before the process through the filter process-inverse filter process in sufficiently bright image area, 25 filters are required in case of 5×5 filter size, and 49 filters are required in case of 7×7 filter size, resulting in increased circuit size.

In the present embodiment, the filter number r is set to full dimension, that is, m smaller than (n×n) (integer to satisfy the relationship of m<(n×n)) for enlarging the filter size of n×n to improve the noise suppression function while preventing the increase in the circuit size. In this case, the filter corresponding to the large eigenvalue is preferentially used to alleviate the influence caused by the reduction in the filter number.

The filter process result (frequency component) derived from the filter coefficient with small eigenvalue corresponding to high frequency may be at the low S/N. Such frequency component has to be reduced. If the filter having the filter coefficient with small eigenvalue is not used, noise is constantly suppressed. The influence to the noise suppression effect caused by the reduction in the filter number may be alleviated.

The weighted mean is performed with respect to the output of the inverse filter section 55 and the original pixel value using the output value of the mean pixel value calculation section 52 so as to further alleviate the influence caused by the reduction of the filter number.

A weighted mean section 61 outputs a value calculated with the following formula (3) using the weighting coefficient s which varies with the mean value Pav outputted from the mean pixel value calculation section 52 as shown in FIG. 17(A) as the pixel value Pout of the filter mask center pixel ((n+1)/2, (n+1)/2).

$$Pout = s \cdot Porg + (1-s) \cdot Pnr \qquad (3)$$

where Pnr denotes a value inputted from the noise suppression circuit 36', s denotes a weighting coefficient ($\leq 1$) in the weighted mean section 61, and Porg denotes the input pixel value (original pixel value) at the filter mask center. In the case where the mean pixel value is large to be bright, the input image value is outputted such that the value of the pixel subjected to the noise suppression process becomes dominant as it becomes darker. This makes it possible to suppress blurring in the bright area as well as suppress the noise easily noticeable in the dark area.

Figure 18:
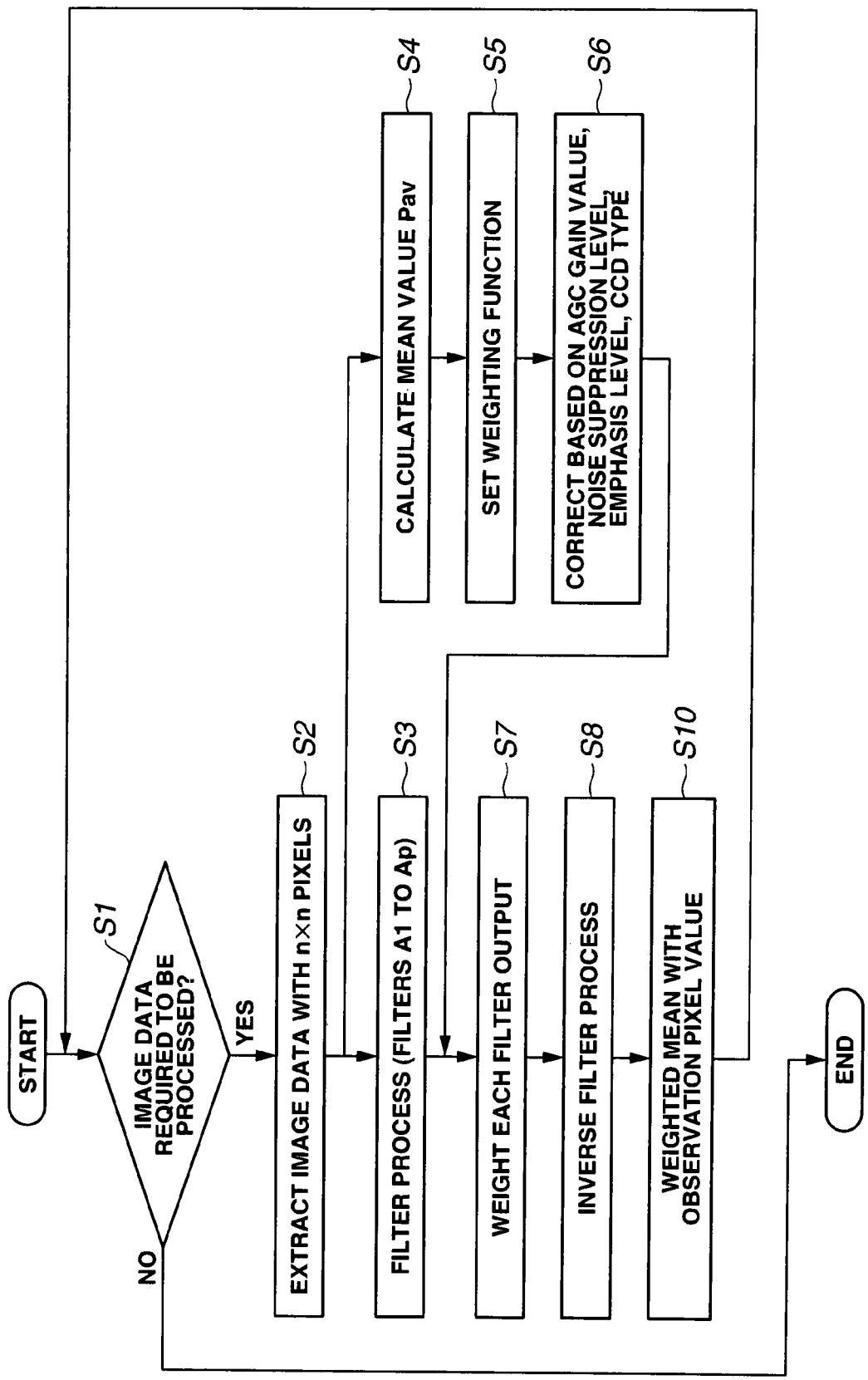
FIG. 18 is a flowchart showing a routine executed in the third embodiment.

FIG. 18 is a flowchart of the operation according to the present embodiment. The routine shown in FIG. 18 includes step S10 to be executed after step S8 as shown in the flowchart of FIG. 10.

Specifically, after the inverse filter process in step S8, the process proceeds to step S110 where the weighted mean is performed with respect to the output of the inverse filter process and the observation pixel value (input pixel value at the filter mask center) using the brightness mean value Pav. Thereafter, the process returns to step S1. Other process is the same as that shown in FIG. 10, and the explanation thereof, thus, will be omitted. In FIG. 18, likewise step S6 shown in FIG. 10, the weighting in the weighting section 53 is corrected based on the AGC gain value and the like according to the second embodiment.

In the configuration of the present embodiment, if the number of the filter r with n×n size is reduced to m, it is possible to output the original signal and to execute the noise suppression process. This makes it possible to downsize the hardware as well as execute the high-speed process.

In the present embodiment, the weighted mean is performed with respect to the output data of the noise suppression circuit with reduced number of filters and the image data of the observation pixel in accordance with the local brightness. This makes it possible to improve the noise suppression function while avoiding deterioration in the sharpness especially in the bright area.

Referring to FIG. 17(A), the weighting coefficient s for the weighted mean is linearly increased from 0 of the brightness mean value Pav. As the modified example of the present embodiment, the gradient of the weighting coefficient s and the intercept with respect to the Pav on the x-axis may be changed in accordance with the noise suppression level which can be arbitrarily set by the operator of the endoscope as shown in FIGS. 17(B) and 17(C).

FIG. 19 shows the relationship between a function (A) of the weighting coefficient s in the weighted mean section 61 and a function (B) of the parameter Cth1 which determines the weighting function characteristics. At the brightness equal to or higher than the mean value Pav_cs where the parameter Cth1 is set to 0 to set the weighting coefficient W in the weighting section 53 to 1, the weighting coefficient s in the weighted mean section 61 is set to 1.0. This makes it possible to alleviate the sharp change in the noise suppression effect in response to the brightness change.

Any other embodiment may be formed by partially combining the aforementioned embodiments.

In the aforementioned embodiments, the light source device 3 illuminates light with the narrow-band wavelength, that is, R2, G2 and B2 in the NBI mode as shown in FIG. 4. The light with two narrow-band wavelengths, for example, G2 and B2 may be used for illumination.

In the aforementioned case, the image data of G and B under the illumination of the light G2 and B2 are subjected to the image process in the noise suppression circuit 36 such that the image data of R, G and B channels are generated from the image data of G and B using the formula (1) in the color conversion circuit 38.

The image data of B are used as the image data of R used in the white balance circuit 34 shown in FIG. 1. A not shown frame memory is disposed between the A/D conversion circuit 32 and the white balance circuit 34 for outputting the image data of B stored in the frame memory to the white balance circuit 34 in place of the image data of R in synchronization with the timing signal of the timing generator 49.

In the NBI mode, the use of two narrow-band lights allows generation of the image for clearly showing the course of blood vessels around the surface layer through the color conversion process and is effective for the diagnosis because of usefulness of the living body information derived from the short wavelength light such as the course of blood vessels around the surface layer of the mucosal tissue.

In the above explanation, the use of the noise suppression circuits 36 and 36' are effective for the NBI mode. The use of the noise suppression circuits 36 and 36' is also effective for the endoscope apparatus for providing the fluorescent observation image to be described in the following fourth embodiment.

In the aforementioned case, a representative fluorescent image and a reflection image with the reflection light are preliminarily picked up to generate the image data as the sample. The eigenvalue and eigenvector with respect to the image data are obtained to prepare the KL transform base filter coefficient, based on which the noise suppression process such as filter process is executed.

The endoscope apparatus may be configured to include a fluorescent mode for observing the fluorescence in addition to the normal mode and the NBI mode such that the noise suppression image process is executed upon selection of the NBI mode as described in the first to the third embodiments, and the noise suppression image process is executed using the filter coefficient and the like corresponding to the fluorescent mode upon selection of the fluorescent mode.

In the aforementioned embodiments, the endoscope apparatus 1 of frame sequential type is employed. However, the endoscope apparatus of synchronous type may be used to temporarily store A/D converted image data of R, G and B in the memory, and read those image data of R, G and B as the color component images of R, G and B sequentially to be converted into the frame sequential image data to allow the noise suppression in the same way as described above. In the case of color separation, the matrix circuit may be operated to perform the conversion into the image data of R, G and B upon generation of the brightness and color difference signals.

The respective embodiments may be applied to the electronic endoscope, the light source device and the video processor of synchronous type.

In the aforementioned explanation, the mean pixel value calculation section 52 as the brightness calculation means calculates the mean value Pav in the pixel size of n×n to be filter processed. It is not limited to the one for calculating the brightness such as the mean value Pav in the local area that is the same as the small area to be filter processed, but includes the configuration for calculating the mean value in the local area including the n×n pixel size, specifically, the local area of the pixel size (n+a)×(n+a) on the assumption that the a is an even number, for example, 2, 4 and the like.

The first to the third embodiments provide the effect for effectively suppressing the noise while alleviating lowering of the contrast.

Fourth Embodiment

A fourth embodiment according to the present invention will be described referring to FIGS. 20 to 22. Background of the present embodiment will be described hereinafter. A fifth embodiment to be described later has the same background as that of the present embodiment.

In Japanese Unexamined Patent Application Publication No. 1-181168, when the difference between the subject pixel value and the mean value of the peripheral pixels is equal to or larger than the predetermined threshold value, the subject pixel value is replaced with the mean value of the peripheral pixels.

In the aforementioned process, if the white spot noise exists in the adjacent pixel, the mean value becomes large and the noise suppression effect cannot be sufficiently obtained.

The noise suppression method using the median filter has been proposed (Japanese Unexamined Patent Application Publication No. 2004-313413), which has the similar disadvantage as described above.

The high-sensitive image pickup device equipped with the charge multiplier mechanism may be used for observing fluorescence, for example to obtain the bright image under the environment with low incident light intensity to the image pickup device. This may multiply not only the image information but also the white spot noise owing to the pixel defect. The use of the high-sensitive image pickup device requires reduction in the influence of especially the white spot noise.

An object of the present embodiment is to provide an (endoscopic) image processor or an endoscope apparatus capable of appropriately suppressing or reducing the white spot noise even if the white spot noise known as the pixel defect of the image pickup device exists adjacent to the observation pixel.

In order to achieve the above object, the image processor has configurations (a) and (b).

(a) The image processor calculates the difference between the subject pixel value of the image data picked up by the image pickup device and the mean value of the peripheral pixel values, and replaces the subject pixel with the mean value of the peripheral pixels if the calculated difference is equal to or larger than a predetermined threshold value. The image processor includes rearrangement means for arranging the peripheral pixels in the order of the large pixel value, and mean value calculation means for calculating the mean value except the maximum pixel value (single or plural) set by the rearrangement means.

(b) The image processor calculates the difference between the subject pixel value of the image data picked up by the image pickup device and the mean value of the peripheral pixel values, and replaces the subject pixel with the mean value of the peripheral pixels if the calculated difference is equal to or larger than a predetermined threshold value. The image processor includes mean value calculation means for calculating the mean value by excluding the single or plural peripheral pixel in the order of large pixel value.

In order to achieve the above object, the endoscope apparatus has following configurations (c) and (d).

(c) An endoscope apparatus includes an endoscope which contains an image pickup device and an image processor which calculates the difference between the subject pixel value of the image data picked up by the image pickup device and the mean value of the peripheral pixel values, and replaces the subject pixel with the mean value of the peripheral pixels if the calculated difference is equal to or larger than a predetermined threshold value. The image processor includes rearrangement means for arranging the peripheral pixels in the order of the large pixel value, and mean value calculation means for calculating the mean value except the maximum pixel value (single or plural) set by the rearrangement means.

(d) An endoscope apparatus includes an endoscope which contains an image pickup device and an image processor which calculates the difference between the subject pixel value of the image data picked up by the image pickup device and the mean value of the peripheral pixel values, and replaces the subject pixel with the mean value of the peripheral pixels if the calculated difference is equal to or larger than a predetermined threshold value. The image processor includes mean value calculation means for calculating the mean value by excluding the single or plural peripheral pixel in the order of large pixel value.

The present embodiment will be described in detail. FIG. 20 is a view showing an entire configuration of an endoscope apparatus 101 equipped with the present embodiment. The endoscope apparatus 101 includes an electronic endoscope 102, a light source device 103, a video processor 104 and an observation monitor 5.

The endoscope apparatus 101 is operated in the normal observation mode and the fluorescent observation mode. The electronic endoscope 102 employs a high-sensitive CCD 25E as a high-sensitive image pickup device with multiplier function (charge multiplier function) within the CCD element instead of the CCD 25 in the electronic endoscope 2 as shown in FIG. 1. An excited light cut filter 106 for cutting the excited light is disposed to the front of the image pickup surface of the high-sensitive CCD 25E. The excited light cut filter 106 serves to cut the reflecting light of the excited light irradiated to the observation target point in the fluorescent observation mode, and to transit the fluorescence wavelength.

The light source device 103 employs a rotary filter 14B including a third filter group for the fluorescent observation instead of the second filter group disposed inside the first filter group for the normal observation in the rotary filter 14 of the light source device 3 shown in FIG. 1.

The video processor 104 allows the CCD driver 29 to apply the CCD drive signal to the high-sensitive CCD 25E, and the control voltage generation circuit 107 to apply the control voltage for determining the value of amplification factor of the high-sensitive CCD 25E.

The output signal of the high-sensitive CCD 25E is inputted to the light modulation circuit 33 via the process circuit 31 and the A/D conversion circuit 32, the control voltage generation circuit 107, and a white spot noise suppression circuit 111 for suppressing the white spot noise. The main portion of the white spot noise suppression circuit 111 is configured as shown in FIG. 21.

The light modulation circuit 33 is operated in cooperation with the control voltage generation circuit 107 such that the image on the observation monitor 5 has the appropriate brightness. The light modulation circuit 33 controls the aperture unit 13 of the light source device 103, and the control voltage generation circuit 107 applies the control voltage for controlling the amplification factor of the high-sensitive CCD 25E in the electronic endoscope 102. The high-sensitive CCD 25E has the amplification factor determined based on the value of the control voltage.

The image data outputted from the A/D conversion circuit 32 are inputted to a subtracter 112 and a selector 113 which form the white spot noise suppression circuit 111 via a not shown delay circuit.

A rearrangement section 114 is activated at the timing when each pixel of the image data is inputted for rearranging 8 peripheral pixels among 9 pixels from M11 to M33 of a mask 115 with 3×3 pixels except the subject pixel M22 at the center in the order from the maximum to the minimum value.

The rearrangement may include the function for calculating at least the maximum value. Seven pixel values except the maximum pixel value Mmax (M1 to M7 shown in FIG. 21) are outputted to the mean value calculation section 116 where the calculated mean value <M> is outputted to the subtracter 112 and the selector 113.

The subtracter 112 subtracts the mean value <M> of the peripheral pixels from the subject pixel M22 (maximum pixel is excluded), and outputs the subtracted value to a comparator 117. The comparator 117 compares the subtracted value with the threshold value applied to the other input end, and controls selection of the selector 113 with the comparison result as the selector signal.

The selector 113 selects the value of the subject pixel M22 or the mean value <M> based on the selector signal so as to be outputted to the synchronization circuit 45 in the next stage as an output signal of the white spot noise suppression circuit 111.

Specifically, when the output value of the subtracter 112 is smaller than the threshold value, it is determined that the subject pixel M22 is not the white spot noise, and the selector 113 outputs the subject pixel M22.

Meanwhile, when the output value of the subtracter 112 is equal to or larger than the threshold value, it is determined that the subject pixel M22 is the white spot noise, and the selector 113 outputs the mean value <M> such that the white spot noise is replaced with the mean value <M> for suppressing the white spot noise.

Figure 20:
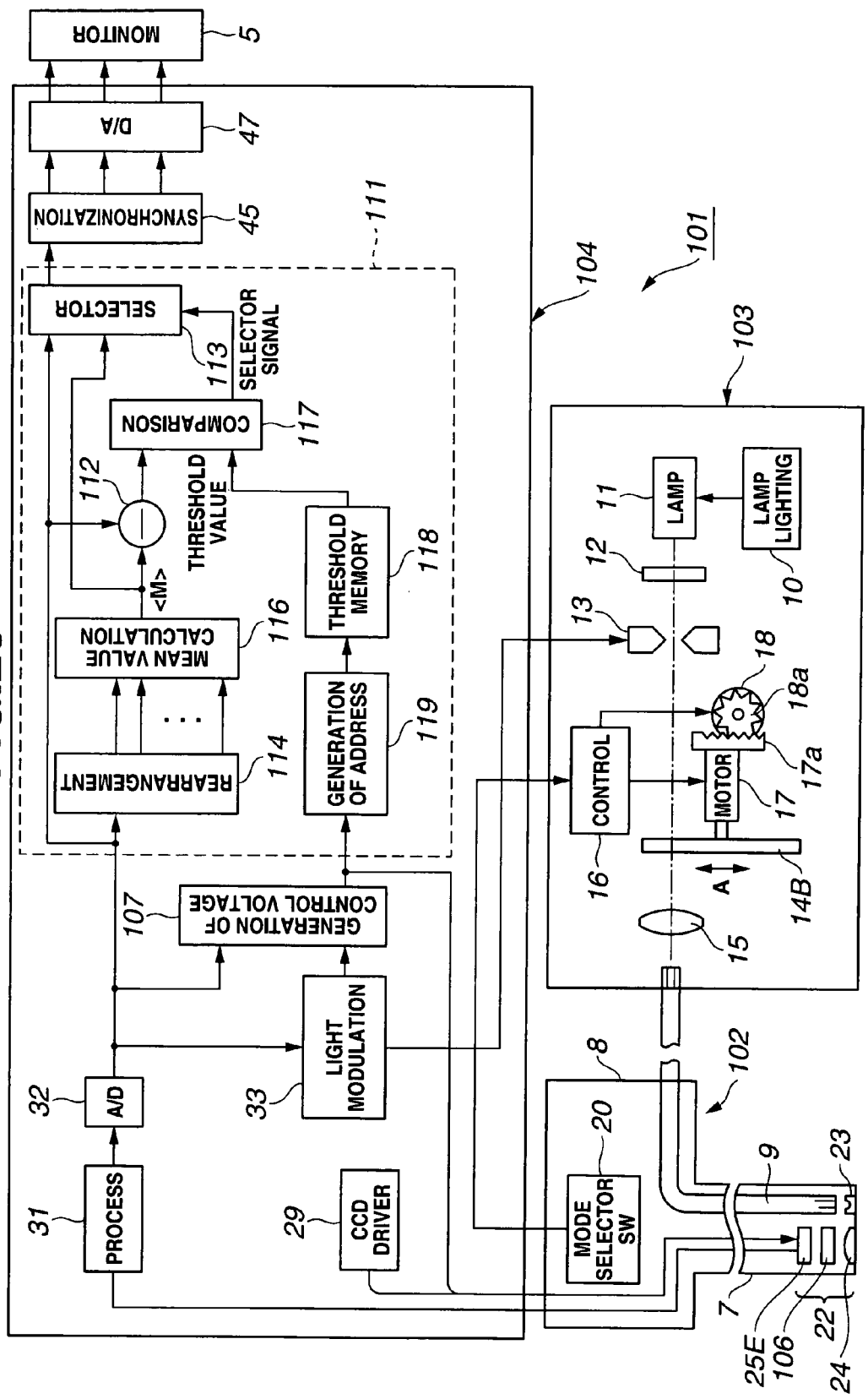
FIG. 20 is a view showing an entire configuration of an endoscope apparatus equipped with a fourth embodiment of the present invention.

The threshold value outputted to the comparator 117 is outputted from a threshold memory 118 which stores the threshold values as shown in FIG. 20.

The threshold memory 118 stores various threshold values corresponding to the different addresses.

An address generation circuit 119 outputs a different address value in accordance with the level of the control voltage outputted from the control voltage generation circuit 107 such that the threshold value corresponding to the control voltage level, that is, the amplification factor of the high-sensitive CCD 25E is outputted to the comparator 117.

As the amplification factor of the high-sensitive CCD 25E increases substantially exponentially in accordance with the control voltage level, the difference between the pixel with no white spot noise and the pixel with the white spot noise, that is, the white spot noise value becomes large as the amplification factor increases.

The amplification factor of the high-sensitive CCD 25E is set to different values in accordance with the control voltage level. In the present embodiment, a plurality of threshold values corresponding to a plurality of amplification factors are preliminarily prepared, and the address generation circuit 119 and the threshold memory 118 are provided for outputting the threshold value corresponding to the set amplification factor such that the appropriate threshold value is selected even if the amplification factor is changed.

The white spot noise suppression circuit 111 is activated in the fluorescent mode for observing the fluorescence, and is not activated in the normal mode. The output signal of the A/D conversion circuit 32 is inputted to the synchronization circuit 45 via the selector 113.

Figures 25, 26:
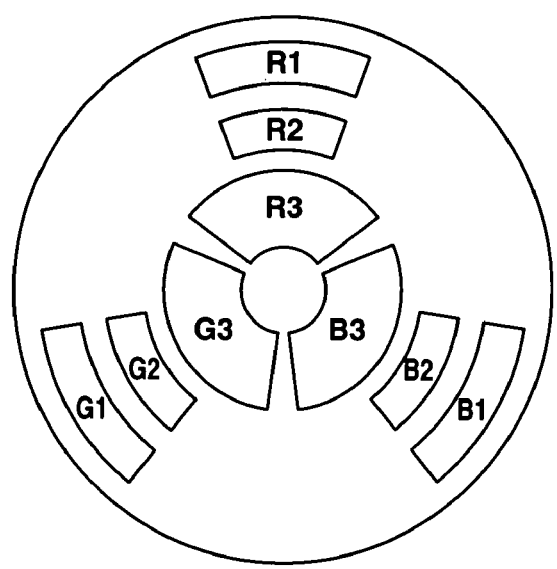
FIG. 25 is a view showing a specific example of pixel values of the pixel to be processed and the peripheral pixels which have been set for detecting the white spot noise.
FIG. 26 is a view showing a configuration of a rotary filter shown in FIG. 20.

In the case where the normal mode is selected by the mode selector switch 20, likewise the first embodiment, the first filter group disposed on the illumination optical path serves to illuminate with the illumination lights of R1, G1 and B1 as shown in FIG. 3. Meanwhile, in the fluorescent mode, the third filter group including R3, G3 and B3 disposed on the illumination optical path as shown in FIG. 26 may be provided with filters each having transmission characteristic of the R2, G2 and B2 as shown in FIG. 4, for example, which receives the fluorescence of the B2 as the excited light. The other R2 and G2 may be used to superpose the reflecting light image with the fluorescent image to be displayed. Only the fluorescent image may be displayed.

The same components as those as described in the first embodiment will be designated with the same codes, and explanations thereof, thus will be omitted.

In the case where the amplification factor of the high-sensitive CCD 25E is set to the large value, the white spot noise becomes especially highly noticeable. The present embodiment is configured to allow the white spot noise suppression circuit 111 to function in the fluorescent mode.

The operation of the white spot noise suppression circuit 111 in the fluorescent mode according to the present embodiment will be described. The operation in the normal mode is the same as the operation as described in the first embodiment having a part of the function such as magnification omitted.

In the fluorescent mode where the third filter group is disposed on the illumination optical path, the excited light is irradiated to the observation subject site. The fluorescence excited and generated by the excited light at the observation subject site is received by the high-sensitive CCD 25E. The excited light reflected on the observation subject site is cut by the excited light cut filter 106 so as not to be received by the high-sensitive CCD 25E.

Figure 21:
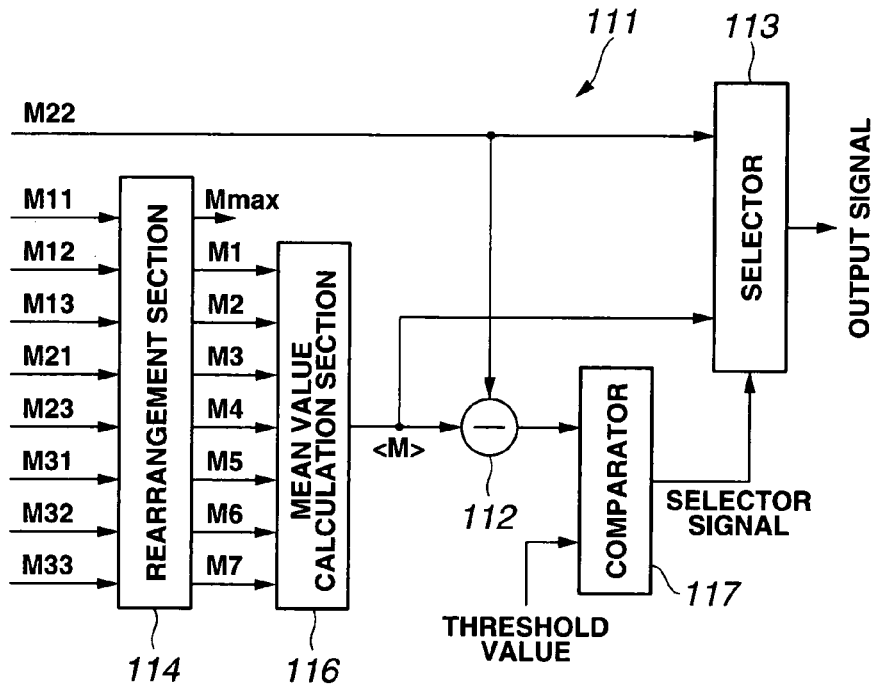
FIG. 21 is a view showing a configuration of a white spot noise suppression circuit.

The image data picked up by the high-sensitive CCD 25E and A/D converted by the A/D conversion circuit 32 are inputted to the white spot noise suppression circuit 111 as shown in FIG. 21. The image data of the subject pixel M22 sequentially inputted to the white spot noise suppression circuit 111 are inputted to the subtracter 112 and the selector 113.

The rearrangement section 114 rearranges the peripheral pixels of the subject pixel M22 in the order of the large pixel value, and outputs the pixels M1 to M7 except the pixel with the maximum value Mmax to the mean value calculation section 116 where the mean value <M> is calculated.

The subtracter 112 subtracts the mean value <M> from the subject pixel M22 so as to be outputted to the comparator 117. The comparator 117 compares the output value with the threshold value.

The mean value <M> is obtained having the maximum pixel Mmax excluded. If the white spot noise exists in the peripheral pixels, the influence of such noise is eliminated. The comparison between the output value of the subtracter 112 and the threshold value in the comparator 117 allows the determination to be appropriately made whether or not the subject pixel M22 has the white spot noise.

In the present embodiment, even if the pixel with the white spot noise exists adjacent to the subject pixel, the determination whether or not the subject pixel M22 includes the white spot noise may be made while being hardly influenced by the white spot noise. The pixel with the white spot noise may be replaced with the appropriate value so as to effectively suppress the white spot noise.

As has been apparent from the aforementioned operation, the rearrangement section 114 may be configured to detect the maximum pixel Mmax among the peripheral pixels without rearranging, and output the pixels except the maximum pixel Mmax to the mean value calculation section 116. In the case where the white spot noise exists in two pixels adjacent to the subject pixel M22, the rearrangement section 114 may be configured to output the pixels except the maximum pixel Mmax and the pixels with the second largest value to the mean value calculation section 116 for calculating the mean value <M>.

In the present embodiment, even if the white spot noise exists in two adjacent pixels, the influence of the white spot noise is not contained in the mean value <M> of the peripheral pixels such that the white spot noise is appropriately corrected.

The present embodiment may be applied to the case where there is a possibility of the deficit pixel or the pixel with considerably small value compared with the normal pixel (hereinafter referred to as the pixel with the black spot noise).

In the aforementioned case, the mean value is calculated by excluding the pixel with minimum value, and the value obtained by subtracting the calculated mean value from the subject pixel value is compared with the threshold value so as to determine with respect to the black spot noise. Depending on the determination result, it is determined whether or not the subject pixel is replaced to be outputted.

In the present embodiment, description has been made in the case of the high-sensitive image pickup device equipped with the amplification function inside the device. However, the present embodiment may be applied to the case where image pickup device equipped with no amplification function inside the device such as the CCD 25 is employed, for example, the AGC circuit 35 is provided for amplification.

A first modified example of the present embodiment will be described. The generally employed frame sequential endoscope apparatus is configured to make a comparison among the subject pixel value, the peripheral pixel values and the mean value of the peripheral pixels with respect to the RGB colors, and determines the pixel having the resultant difference equal to or larger than the predetermined threshold value as the white spot noise such that the subject pixel value is replaced with the mean value of the peripheral pixels.

In the case where a certain color among the three colors of RGB is far brighter than the peripheral pixels, for example, boundary information of the structure, the random noise and the like, the pixel of the bright color is determined as the white spot noise and corrected. In this case, a large amount of pixels other than the white spot noise are corrected, thus making the image further blurred.

In the modified example, the difference between the subject pixel value and the mean value of the peripheral pixels is obtained with respect to the RGB colors, and the resultant difference is compared with the predetermined threshold value. If the difference is equal to or larger than the threshold value, the case where all of the RGB colors have the difference equal to or larger than the threshold value is only determined as being the white spot noise. Such image is replaced with the mean value of the peripheral pixels in the endoscope apparatus for replacing the subject pixel value with the mean value of the peripheral pixels.

In the case where predetermined gains are applied to the RGB colors, respectively such as the color balance value, the threshold values may be set in consideration for the respective gain values for the respective colors. The threshold value may be changed in accordance with the amplification factor of the high-sensitive image pickup device.

Figure 23:
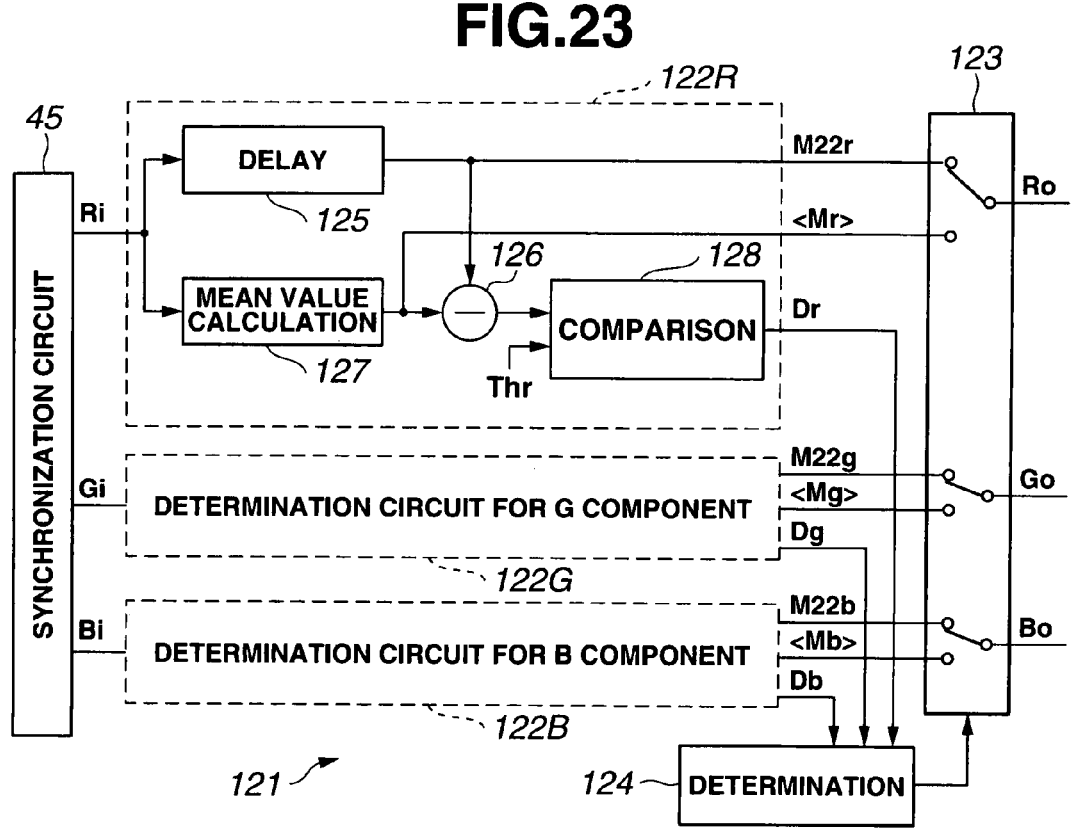
FIG. 23 is a view showing a configuration of the white spot noise suppression circuit in a first modified example.

In the modified example, the image data of the A/D conversion circuit of the configuration shown in FIG. 20 are directly stored in the synchronization circuit 45 temporarily so as to suppress the white spot noise with respect to the R image data, G image data and B image data read therefrom through the white spot noise suppression circuit 121 as shown in FIG. 23.

Referring to FIG. 23, the R image data Ri, G image data Gi and B image data Bi which are inputted from the synchronization circuit 45 to the white spot noise suppression circuit 121 are inputted to R component determination circuit 122R, G component determination circuit 122G and B component determination circuit 122B, respectively.

Output signals from the R component determination circuit 122R, the G component determination circuit 122G and the B component determination circuit 122B are inputted to the selector 123, and to the determination circuit 124 for determining whether or not each of the three colors is equal to or larger than the threshold value.

An output signal of the determination circuit 124 serves to control selection of the selector 123 which outputs R output image data Ro, G output image data Go and B output image data Bo as output signals of the white spot noise suppression circuit 121.

The subject pixel M22$r$ of the R image data Ri is inputted to the subtracter 126 and the selector 123 via the delay circuit 125 which forms the R component determination circuit 122R.

The peripheral pixel Mijr (each of i and j is an arbitrary integer from 1 to 3 except the subject pixel M22 with i=j=2, and the suffix r denotes the pixel of R component) of the subject pixel M22$r$ is inputted to the mean value calculation section 127 where the mean value <Mr> is calculated.

The calculated mean value <Mr> is inputted to the subtracter 126 and the selector 123. The subtracter 126 subtracts the mean value <Mr> from the value of the subject pixel M22$r$, and the subtracted output is inputted to the comparator 128 so as to be compared with the R component threshold value Thr.

A comparison result Dr in the comparator 128 is inputted to the determination circuit 124.

Configurations of the G component determination circuit 122G to which the G image data Gi are inputted, and the B component determination circuit 122B to which the B image data Bi are inputted are basically the same as that of the R component determination circuit 122R except that the threshold value Thr is changed to Thg and Thb, respectively.

The G component determination circuit 122G sends the output of the subject pixel M22$g$ and the mean value <Mr> to the selector 123, and sends the comparison result Dg to the determination circuit 124.

The B component determination circuit 122B sends the output of the subject pixel M22$b$ and the mean value <Mb> to the selector 123, and sends the comparison result Db to the determination circuit 124.

The determination circuit 124 allows the selector 123 to output the mean values <Mr>, <Mg> and <Mb> only in the case where the comparison results Dr, Dg and Db are all equal to or larger than the corresponding threshold values Thr, Thg and Thb. In the cases other than the above-mentioned case, the subject pixels M22$r$, M22$g$ and M22$b$ are outputted.

The determination circuit 124 determines that the subject pixel M22 is the one with the white spot pixel only when the following relationships are satisfied simultaneously such that the subject pixel values are replaced with the mean values to be outputted. In the cases other than that, the aforementioned replacement is not performed.

$$|M22r-<Mr>| \geq Thr$$

$$|M22g-<Mg>| \geq Thg$$

$$|M22b-<Mb>| \geq Thb$$

In the modified example, the pixel having all the colors equal to the threshold values may only be extracted. The determination may be made by detecting the pixel value having all the colors distinguished as the white spot noise. Correction of the pixel having a single color distinguished such as the boundary information of the structure and the random noise is limited to prevent the image to be made blurred owing to the excessive correction. This makes it possible to improve detection of the white spot noise and the correction function.

A second modified example will be described. A high-sensitive image pickup device equipped with the charge multiplier mechanism is employed for the purpose of obtaining the bright image under the environment where the incident light intensity to the image pickup device is low for the fluorescent observation, for example. This may multiply not only the image information but also the white spot noise owing to the pixel defect.

The generally employed white spot noise correction means is configured to compare the subject pixel value with the peripheral pixel value with respect to each of the RGB colors of the endoscope of frame sequential type, and to determine the pixel having the resultant difference equal to or larger than the predetermined threshold value as the white spot noise such that the subject pixel is replaced with the peripheral pixel value. The aforementioned process detects the halation boundary area as the white spot noise so as to be corrected. As a result, the pixel is unnecessarily corrected to make the image further blurred.

In the modified example, the halation area is recognized (determined), and the area determined as the halation area is not subjected to the white spot noise correction. The method for making the determination with respect to the halation area includes the following processes.

A. The determination is made based on the pixel value of the subject pixel. Specifically, the determination with respect to the halation is made based on the judgment with respect to the maximum pixel value. In this case, the white spot noise has the pixel value slightly larger than that of the peripheral pixels, but is not the maximum value.

B. In the case where the pixel with the maximum value exists in the area including the subject pixel and a plurality of pixels adjacent thereto, the halation area is determined.

Figure 24:
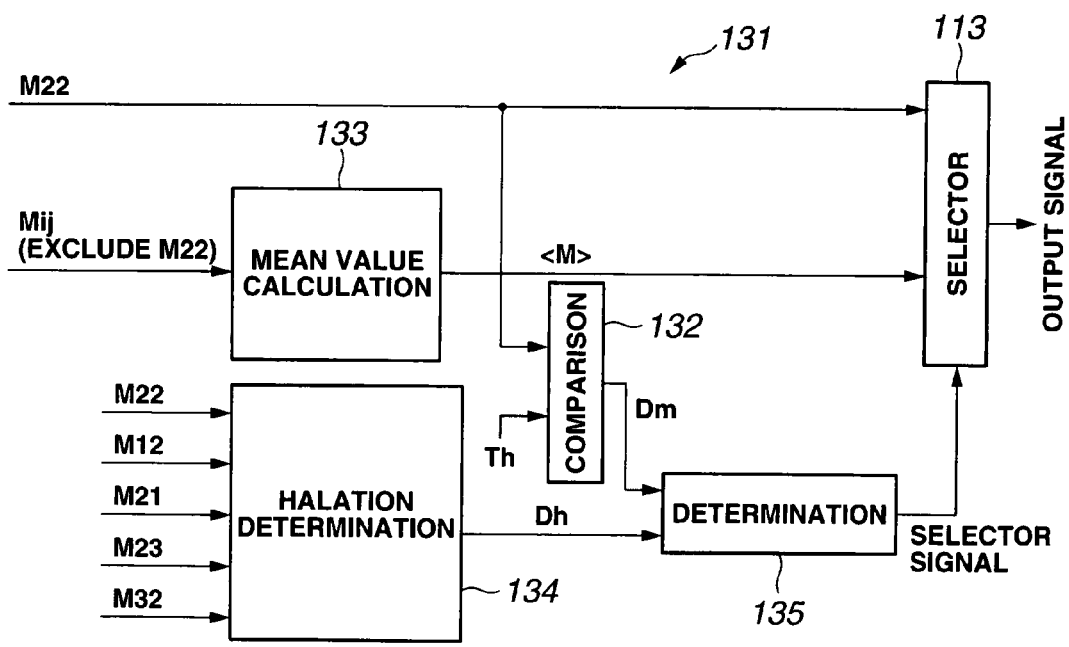
FIG. 24 is a view showing a configuration of the white spot noise suppression circuit in a second modified example.

C. The process A may fail to correct the noise in the case where the amplification factor is large which makes the value of the pixel with the white spot noise maximum (equivalent to the saturated pixel). For the purpose of avoiding the aforementioned problem, in the case where the halation pixel is determined based on the single pixel only, it is determined as the white spot (noise) so as to be corrected. FIG. 24 shows the configuration of the white spot noise suppression circuit 131 equipped with the means for determination with respect to halation.

Figure 22:
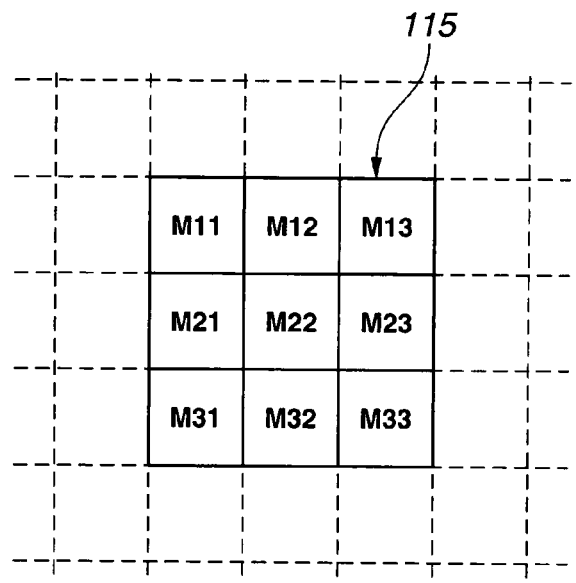
FIG. 22 is a view showing a mask set to contain the peripheral pixel with the pixel to be processed at the center for detecting the white spot noise.

When the mask including the peripheral pixels M11 to M33 that surround the subject pixel M22 as shown in FIG. 22 is set (except M22), the signal of the target pixel M22 is inputted to the selector 113 and the comparator 132 so as to be compared with the threshold value Th.

The signal of the peripheral pixel Mij (each of i and j denotes an integer from 1 to 3 except i=j=2) that surrounds the subject pixel M22 is inputted to the (peripheral pixel) mean value calculation section 133 where the mean value <M> of the peripheral pixels Mij is calculated and inputted to the selector 113.

In the modified example, the signals corresponding to the specific peripheral pixels M12, M21, M23 and M32 (except M22) among the peripheral pixels M11 to M33 surrounding the subject pixel M22 with the diagonally adjacent pixels excluded are inputted to the halation determination circuit 134 where the determination is made with respect to the pixel in the halation area.

The determination result Dh in the halation determination circuit 134 is inputted to a determination circuit 135 together with the comparison result Dm in the comparator 132. The determination output in accordance with the aforementioned results is used as the selector signal for controlling selection of the selector 113.

In the halation determination circuit 134, the determination is made with respect to any one of the following D to F. The following explanation will be made with respect to 8-bit of the image data (0 to 255) for the respective pixels.

D. If the center pixel M22 has the maximum pixel value of 255, it is determined to be in the halation area.

E. If the center pixel M22 has the maximum pixel value of 255, and at least one pixel of those adjacent to the center pixel M22 (only in the lateral and vertical directions, and except the diagonal direction) becomes maximum of 255, it is determined that the center pixel M22 is in the halation area.

F. If the center pixel M22 has the maximum pixel value of 255, and the peripheral pixels do not have the maximum values of 255, it is determined that the center pixel M22 is not in the halation area.

If the halation is determined in the halation determination circuit 134 based on the determination result Dh, the determination circuit 135 outputs the selector signal to the selector 113 for outputting the center pixel M22. If it is determined that the determination result Dh in the halation determination circuit 134 is not halation, and the comparison result Dm in the comparator 132 is equal to or larger than the threshold value, the selector signal for outputting the mean value <M> is outputted to the selector 113. If it is determined that the determination result Dh is not in the halation area, and the comparison result Dm is equal to or smaller than the threshold value, the selector signal for outputting the center pixel M22 is outputted to the selector 113.

For example, FIG. 25 shows an example of values of the target pixel and the peripheral pixels surrounding the observation pixel to be inputted to the white spot noise suppression circuit 131. As this example corresponds to the determination D or E, the center pixel is determined to be halation, and the center pixel M22 with data value of 255 is directly outputted without selecting the selector 113 with the selector signal.

The determination method may be changed in accordance with the amplification factor to the high-sensitive CCD 25E. Specifically, if the amplification factor is equal to or smaller than the predetermined threshold value, the determination circuit 135 makes the determination with respect to the halation pixel with the method D or E. If the amplification factor is larger than the threshold value, the determination is made with the method F as described above.

According to the modified example, the halation area is excluded when the white spot noise correction is made. The clear image may be provided without the unnecessary pixel blurred.

Fifth Embodiment

A fifth embodiment according to the present invention will be described referring to FIGS. 27 to 31. It is an object of the present embodiment to provide an image processor and the endoscope apparatus capable of correcting the pixel defect in the image pickup device while avoiding lowering of S/N in the fluorescent observation image even if a plurality of endoscopes each having different characteristic to allow the fluorescent observation are connected to a pair of the light source device and the image process apparatus (specifically, video processor).

In order to achieve the aforementioned object, the image processor has the following configurations (e) and (f).

(e) The image processor includes:

image process means which contains first and second image pickup devices each having a filter with different transmission wavelength characteristic used for a fluorescent observation so as to pick up a subject image by accumulating the charge, to which first and second endoscopes each containing first and second storage means for storing information with respect to an accumulation time are selectively connected such that the difference between the subject pixel value of the image data picked up by the first and the second image pickup devices and a mean value of peripheral pixel values is derived, the resultant difference is compared with a predetermined threshold value, and the subject pixel is replaced with the mean value of the peripheral pixels when the difference is equal to or larger than the threshold value;

rearrangement means for rearranging the peripheral pixels in the order of the large pixel value, and mean value calculation means for calculating the mean value except the maximum pixel value (single or plural) set by the rearrangement means; and means for changing process parameter with respect to the image process based on the information with respect to the accumulation time in the storage means.

(f) The image processor includes:

image process means which contains first and second image pickup devices for picking up the subject image by accumulating the charge, each having a filter with different transmission wavelength characteristic for the fluorescent observation, to which connect first and second endoscope each containing first and second storage means for storing information with respect to the accumulated time are selectively connected such that the difference between the subject pixel value of the image data picked up by the first and the second image pickup devices and the mean value of the peripheral pixel values is derived, the resultant difference is compared with a predetermined threshold value, and the subject pixel is replaced with the mean value of the peripheral pixels when the difference is equal to or larger than the threshold value;

mean value calculation means for excluding at least a peripheral pixel in the order of large pixel value to calculate the mean value; and means for changing process parameters with respect to the image process based on the information with respect to the accumulated time in the storage means.

For the purpose of achieving the aforementioned object, the endoscope apparatus includes the following configurations (g) to (k).

(g) An endoscope apparatus includes:

first and second endoscopes each having a filter with different transmission wavelength characteristic for the fluorescent observation, and containing first and second image pickup devices for picking up the subject image by accumulating the charge;

first and second memory means each provided in the first and the second endoscopes, respectively for storing the information with respect to an accumulated time;

illumination means for illuminating the subject with an illumination light via the first and the second endoscopes; and image processor for deriving and comparing a difference between the subject pixel value of the image data picked up by the first and the second image pickup devices and a mean value of peripheral pixel values with a predetermined threshold value, and replacing the subject pixel with the mean value of the peripheral pixels when the difference is equal to or larger than the threshold value, wherein the image processor includes rearrangement means for rearranging the peripheral pixels in the order of the large pixel value, mean value calculation means for calculating the mean value by excluding the maximum pixel value (single or plural) set in the rearrangement means, and means for changing the process parameters with respect to the image process based on the accumulated time information in the memory means.

(h) An endoscope apparatus includes:

first and second endoscopes each having a filter with different transmission wavelength characteristic for the fluorescent observation, and containing first and second image pickup devices for picking up the subject image by accumulating the charge;

first and second memory means each provided in the first and the second endoscopes, respectively for storing the information with respect to an accumulated time;

illumination means for illuminating the subject with an illumination light via the first and the second endoscopes; and image processor for deriving and comparing a difference between the subject pixel value of the image data picked up by the first and the second image pickup devices and a mean value of peripheral pixel values with a predetermined threshold value, and replacing the subject pixel with the mean value of the peripheral pixels when the difference is equal to or larger than the threshold value, wherein the image processor includes mean value calculation means for calculating the mean value by excluding at least one of the peripheral pixels in the order of the large value, and means for changing the process parameters with respect to the image process based on the accumulated time information in the memory means.

(i) In the endoscope apparatus according to (h), the process parameter is the threshold value in the noise suppression means.

(j) In the endoscope apparatus according to (h), the accumulated time accumulated by the first or the second image pickup devices when the illumination means illuminates at least one illumination light is stored in the first and the second memory means, respectively.

(k) In the endoscope apparatus according to (h), the accumulated time accumulated by the first and the second image pickup devices when the illumination means illuminates with an illumination light for obtaining a reflecting light image is stored in the first and the second memory means.

Figure 27:
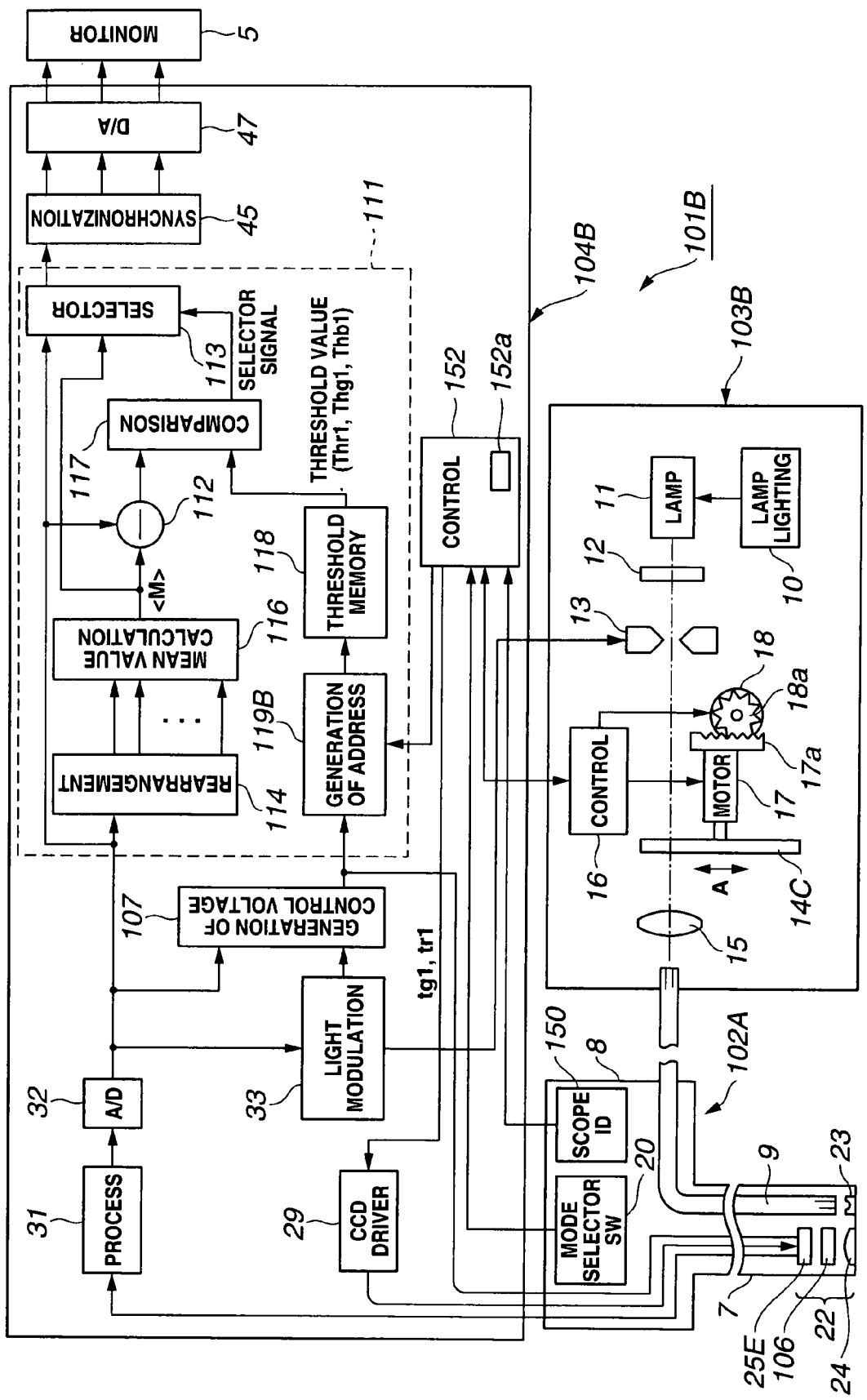
FIG. 27 is a view showing an entire configuration of an endoscope apparatus equipped with a fifth embodiment of the present invention.
Figure 30:
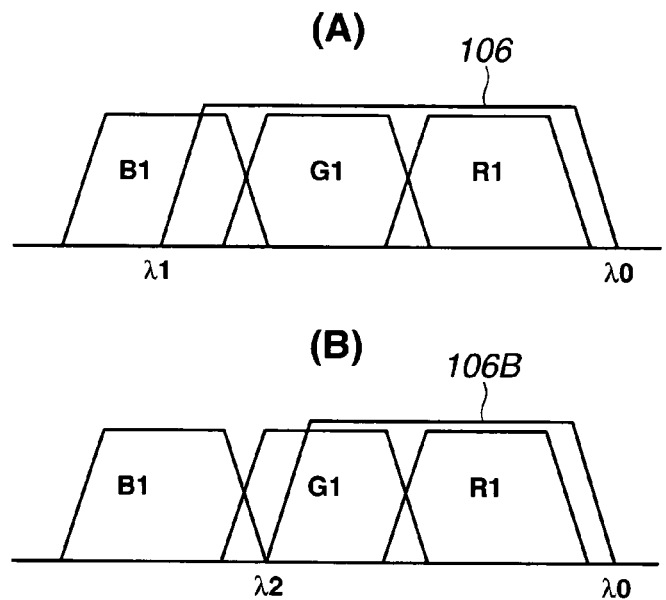
FIG. 30 is a view schematically showing the transmissivity characteristics of the excited light cut filters respectively used for the first and the second electronic endoscopes relative to the wavelength area of the illumination light for the normal observation.

FIG. 27 is a view showing an endoscope apparatus 101B equipped with the image processor according to the fifth embodiment. The endoscope apparatus 101B includes an electronic endoscope 102A as a first electronic endoscope, an electronic endoscope 102B as a second electronic endoscope shown in FIG. 28, a light source device 103B, a video processor 104B as the image processor according to the present embodiment, and an observation monitor 5. As the configuration of the present embodiment is similar to that of the fourth embodiment, the same component as those described in the fourth embodiment are designated with the same codes, and explanations thereof, thus will be omitted.

The electronic endoscope 102A is configured by adding a scope ID generation circuit 150 for generating identification information unique to the electronic endoscope 102A to the electronic endoscope 102 in the fourth embodiment as shown in FIG. 20.

The second electronic endoscope 102B shown in FIG. 28 is configured by adding image pickup means for the normal observation to the electronic endoscope 102A shown in FIG. 27.

The electronic endoscope 102A shown in FIG. 27 includes one CCD 25E operated both for the normal observation and the fluorescent observation. Meanwhile, the electronic endoscope 102B shown in FIG. 27 includes a CCD 25F for the normal observation and a CCD 25E for the fluorescent observation.

The CCD 25F for the normal observation is disposed at the image-forming position on an objective lens 24F without the excited light cut filter 106. The objective lens 24F having the same characteristic as that of the objective lens 24 may be employed.

Output signals of the CCD 25E and the CCD 25F are inputted to the process circuit 31 of the video processor 104B via a selector switch 151 having the contact selected with the mode selector switch 20. In the present embodiment, the CCD 25E and the CCD 25F are driven by a common CCD driver 29.

The excited light cut filter 106 disposed to the front of the image pickup surface of the CCD 25E of the electronic endoscope 102A and the excited light cut filter 106B disposed to the front of the image pickup surface of the CCD 25E of the electronic endoscope 102B are set to have different characteristics with respect to the transmission range as shown in FIGS. 29(A) and 29(B).

In the electronic endoscope 102B, the CCD 25E is used only for the fluorescent observation. Unlike the wavelength band of the excited light Ex, the excited light cut filter 106B is set to have the characteristic to transmit the wavelength range of G2 and R2 for obtaining the reflection light image as shown in FIG. 29(B). Specifically, the wavelength band from the wavelength $\lambda 2$ to $\lambda 0$ longer than the wavelength R2 is allowed to transmit. The wavelength of $\lambda 2$ is set to be slightly shorter than the wavelength band of G2.

In the electronic endoscope 102A, the CCD 25E is used for both the normal observation and the fluorescent observation. The excited light cut filter 106 disposed to the front of the image pickup surface of the CCD 25E transmits the light with the wavelength band from the wavelength λ1 to λ0 as shown in FIG. 29(A). The wavelength of λ1 has the wavelength band shorter than that of G2 such that the relationship λ1<λ2 is established.

The excited light Ex, and the illumination lights G2 and R2 shown in FIG. 29 show the wavelength band of the frame sequential illumination light radiated from the light source device 103B in the fluorescent observation mode.

In the present embodiment, a first fluorescent image lu1 derived from the first electronic endoscope 102A is synthesized with first reflecting light images r1 and g1 picked up under the illumination light of R2 and G2 in the narrow-band with lowered illumination light intensity in the video processor 104B and displayed on the monitor 5 for the fluorescent observation. Likewise the second fluorescent image lu2 derived from the second electronic endoscope 102B is synthesized with second reflecting light images r2 and g2 picked up under the illumination light with the narrow-band with lowered illumination light intensity in the video processor 104B for the fluorescent observation such that the fluorescent observation image is displayed on the observation monitor 5.

As the first and the second electronic endoscopes have the same transmission factor of the excited light cut filter which transmits the illumination light R2 in the wavelength band, each signal level of the first reflecting light images r1 and r2 when picking up the first subject becomes equivalent. In the first and the second electronic endoscopes, the transmission factor of the excited light cut filter is the same in the wavelength band of the illumination light G2. Accordingly, the signal level of the first reflecting light images g1 and g2 becomes equivalent when picking up the same subject.

As shown in FIG. 30(A), for the normal observation, the excited light cut filter 106 is set to partially transmit the illumination light in the broad-band B1 such that the color signal which has been picked up under the illuminated light of B1 with the broad-band is provided. Meanwhile, the excited light cut filter 106B is set not to transmit the illumination light of B1 for the normal observation as shown in FIG. 30(B). That is, the excited light cut filter 106 has the transmission wavelength range set to be broader than that of the excited light cut filter 106B.

In the case where the same subject is subjected to the fluorescent observation in the fluorescent observation mode with the common light source device 103B, the signal level of the first fluorescent image lu1 picked up by the CCD 25E with the excited light cut filter 106 is higher than that of the second fluorescent image lu2 picked by the CCD 25E with the excited light cut filter 106B. In other words, when the fluorescent observation is conducted in the fluorescent observation mode with the common light source device 103B, the output level of the CCD 25E differs in the cases between the electronic endoscope 102A and the electronic endoscope 102B.

In the present embodiment, the video processor 104B is provided with process parameter change means (specifically, means for changing the image pickup period or the accumulated time) for coinciding the signal level of the reflecting light image with that of the fluorescent image such that the appropriate fluorescent observation image is generated while avoiding deterioration in the S/N irrespective of the difference in the characteristics between the excited light cut filters.

The light source device 103B employed in the endoscope apparatus 101B is formed by providing the rotary filter 14C equipped with the excited light filter for generating the excited light Ex as shown in FIG. 29(A) instead of the B2 filter 14b2 of the rotary filter 14 in the light source device 3 according to the first embodiment. That is, in the fluorescent observation mode, the light source device 103B radiates illumination lights of R2, G2, and excited light Ex sequentially and in the normal observation mode, the light source device 103B radiates illumination lights of R1, G1, B1 sequentially.

The video processor 104B employed in the endoscope apparatus 101B is formed by partially modifying the video processor 104 according to the fourth embodiment shown in FIG. 20.

The video processor 104B according to the present embodiment appropriately corrects the pixel defect such as the white spot noise, and executes the image process for generating the quality image with less noise in both cases where the electronic endoscope 102A employs a single CCD 25E used for the normal observation and the fluorescent observation, and where the electronic endoscope 102B employs the CCD 25F and CCD 25E for the normal observation and the fluorescent observation, respectively. The video processor 104B is formed by adding the control unit 152 to the video processor 104 shown in FIG. 20. The control unit 152 controls the CCD driver 29 and the address generation circuit 119 in accordance with the information with respect to the reflecting light written into the scope ID generation circuit 150, and the fluorescent accumulation time.

For example, the control unit 152 reads the information with respect to the reflection light and the fluorescent storage time from the scope ID generation circuit 150 upon initial selection to the fluorescent observation mode (start-up timing is available) so as to be stored in the memory 152a within the control unit 152.

When the user selects the fluorescent observation mode, the control unit 152 reads the information with respect to the time for image pickup of the reflection light image and the fluorescent light image (specifically, the accumulated time) from the memory 152a for controlling the accumulated time as the process parameter to the CCD driver 29, that is, electronic shutter by the CCD 25E.

Referring to FIG. 27, in the case where the electronic endoscope 102A is connected to the video processor 104B, the control unit 152 allows the CCD driver 29 to control the image pickup time for illumination with the illumination lights of R2 and G2 (image pickup of the reflection light image) to the values tr1 and tg1, respectively, and to control the image pickup time for irradiation of the excited light Ex (image pickup of the fluorescent light image) to the value tb1.

Meanwhile, in the case where the electronic endoscope 102B is connected to the video processor 104B, the control unit 152 allows the CCD driver 29 to control the image pickup time for illumination with the illumination lights of R2 and G2 to the values tr2 (<tr1) and tg2 (<tg1), respectively and to control the image pickup time for irradiation of the excited light Ex (image pickup of the fluorescent light image) to the value tb2 (=tb1).

As the excited cut filters 106 and 106B for the fluorescent image pickup respectively employed in the electronic endoscopes 102A and 102B have different characteristics, the signal levels (brightness) of the fluorescent images lu1 and lu2 resulting from the image pickup of the same subject are different but the signal levels (brightness) of the reflecting light images r1, g1, and r2 and g2 resulting from the irradiation of the red band light are the same. The balance of the signal levels among the fluorescent observation images formed by synthesizing the fluorescent image and the reflection light image becomes different.

In the present embodiment, when the image pickup time for picking up of the reflection light image is adjusted in accordance with the characteristic of the endoscope (excited light cut filter) (based on the information with respect to the accumulated time preliminarily stored in the scope ID generation circuit 150) such that the signal level (brightness) of the reflection light image coincides with the signal level (brightness) of the fluorescent image when the reference subject image is picked up. This makes it possible to appropriately balance the signal levels (brightness) among the images.

When the image pickup is performed under the weak fluorescence, lowering of the S/N of the fluorescent image caused by the reduction in the image pickup time may be suppressed by preventing reduction in the time for image pickup.

As the excited light cut filters 106, 106B employed for the fluorescent image pickup means in the electronic endoscopes 102A and 102B have different characteristics, the fluorescent images $1u1$ and $1u2$ derived from picking up of the same subject have different values of the brightness, but the reflecting light images r1, g1 and r2, g2 derived from irradiation of the red band light have the same values of the brightness. Accordingly, the balance of the brightness among the respective images derived from synthesizing the fluorescent image and the reflecting light image becomes different.

In the present embodiment, when the brightness of the reflection light image is coincided with that of the fluorescent image, the time for the image pickup device for picking up the image is adjusted (based on the electronic shutter information preliminarily stored in the scope ID generation circuit 150) in accordance with the characteristic of the endoscope (excited light cut filter) upon the pickup of the reflection light image so as to appropriately balance the brightness.

In the above description, the information with respect to the accumulation time of the reflection light and the fluorescence is written in the scope ID generation circuit 150. However, the information with respect only to the time for accumulating the reflection light may be written. The control unit 152 may be configured to store the information with respect to the time for accumulating the reflection light in the memory 152a, and to allow a predetermined accumulation time as the information with respect to the time for accumulating the fluorescence to be preliminarily stored in the memory 152a without using the electromagnetic endoscope connected to the video processor 104B.

The scope generation circuit 150 may be configured to generate the characteristic information with respect to the excited light cut filter 106 or 106B, and the control unit 152 may be configured to store the information with respect to the time for accumulating the reflection light and the fluorescence in accordance with the characteristic information in the memory 152a or the like.

The scope ID generation circuit 150 may be configured to generate the scope ID information, and the control unit 152 may be configured to store the information with respect to the time for accumulating the reflection light and the fluorescence used in the scope ID at the side of the video processor 104B in the memory 152a or the like.

As the generally employed image process for correcting the pixel defect does not make consideration for the pixel value of the pixel defect which changes depending on the image pickup time, the correction has not been appropriate made. In the present embodiment, the threshold as the process parameter may be changed to appropriately perform the correction.

According to the present embodiment, in the case where the image pickup signal derived from the fluorescent image picked up under the reflection light image with R2 and G2 and the excited light Ex to the address generation circuit 119 is inputted frame sequentially to the comparator 117 of the white spot noise suppression circuit 111 in the fluorescent observation mode, the control unit 152 controls three threshold values read from the threshold memory 118 so as to be applied to the other input end of the comparator 117. Referring to FIG. 27, in the case where the electronic endoscope 102A is connected to the video processor 104B, when the output signal of the subtractor 112 based on the first reflection light images r1, g1 and the fluorescent image lu1 are sequentially inputted to one input end of the comparators 117, and the threshold values applied to the other input end of the comparator 117 are set to Thr1, Thg1 and Thb1, the control unit 152 controls to establish the relationships of Thb1>Thr1, and Thb1>Thg1, respectively.

In the case where the fluorescent image pickup is performed, the amplification factor of the CCD 25E is set to be higher than that of the CCD 25E for the reflection light image pickup. If the white spot noise exists, the signal level is increased owing to the white spot noise. In the aforementioned case, when the signal resulting from the fluorescent image pickup is inputted to the comparator 117, the control unit 152 controls such that the corresponding threshold value Thb1 is set to be higher than the threshold values Thr1 and Thg1.

In the electronic endoscope 102B, the threshold values to be inputted to the comparator 117 are set to be Thr2, Thg2 and Thb2. In this case, the control unit 152 controls so as to establish the relationships of Tthb2>Thr2, and Thb3>Thg2, respectively. The aforementioned setting is made in the same manner as in the case of the threshold value Thb1 and the like.

In the case where the white spot noise exists in the CCD 25E, when the time for image pickup performed by the CCD 25E is short, the signal level is reduced owing to the white spot noise. The control unit 152 sets the relationship of Thr1>Thr2 corresponding to the relationship of tr1>tr2. Similarly, the control unit 152 sets the relationship of Thg1>Thg2 corresponding to the setting of the relationship tg1>tg2.

In the first electronic endoscope 102A and the second electronic endoscope 102B, the amplification factor and the image pickup time of the CCD 25E for the fluorescent observation are set to be the same values. The control section 152, thus, sets the relationship of Thb1=Thb2.

The address generation circuit 119B generates the address value in accordance with the information with respect to the time for accumulation of the reflection light and fluorescence inputted from the control section 152 to be stored in the memory 152a, and the control voltage level outputted form the control voltage generation circuit 107 and switches the threshold value inputted to the comparator 117 from the threshold memory 118.

The fourth embodiment is configured to control selection of the illumination light of the light source device 103 with an output signal generated by operating the mode selector switch 20. In the present embodiment, the operation signal generated by the mode selector switch 20 is inputted to the control unit 152.

The control unit 152 sends the signal for mode selection to the control circuit 16 of the light source device 103B for the mode selection such that the control circuit 16 executes the corresponding control.

A function of the present embodiment will be described. Assuming that the second electronic endoscope 102B is connected to the light source device 103B and the video processor 104B, the control unit 152 controls to illuminate and execute the signal process in the normal observation mode when it is started up upon turning power ON. In the normal observation mode, the light source device 103B radiates illumination lights R1, G1 and B1 sequentially such that the image pickup is performed by the CCD 25F under the illumination lights. In this case, the control unit 152 does not allow the operation of the control voltage generation circuit 107 and the white spot noise suppression circuit 111 as well. In this case, the output signal of the A/D conversion circuit 32 in the video processor 104B is inputted to the synchronization circuit 45 through the white spot noise suppression circuit 111.

The operation in the aforementioned case becomes the same as that of the normal observation mode in the electronic endoscope of the normal frame sequential type. Meanwhile, when the observation mode is selected to the fluorescent observation mode in response to the operation of the mode selector switch 20, the control unit 152 stores the information with respect to the accumulation time which has been read from the scope ID generation circuit 150 in the memory 152a. Based on the information with respect to the accumulation time stored in the memory 152a, the electronic shutter time of the CCD 25E, that is, the aforementioned image pickup times tr2 and tg2 are controlled.

In the fluorescent observation mode, the control unit 152 activates the white spot noise suppression circuit 111. In the case where the output signal of the subtractor 112 based on the second reflection light images r2, g2 and the output signal of the fluorescent image lu2 are sequentially inputted to one input end of the comparator 117, the control unit 152 sets the threshold values applied to the comparator 117 in the white spot noise suppression circuit 111 as the Thr2, Thg2 and Thb2 as being inputted to the other input end of the comparator 117. In the aforementioned case, the control unit 152 controls to establish the relationships Thb2>Thr2 and Thb2>Thg2.

In the case where the first electronic endoscope 102A is connected to the light source device 103B and the video processor 104B in place of the second electronic endoscope 102B, the same operation as the one derived from the replacement of the number 2 of the code, for example, lu2 with the number 1 may be obtained.

In this case, the first electronic endoscope 102A and the second electronic endoscope 102B are set to establish the relationship tr1>tr2. This makes it possible to display the first fluorescent image lu1 or the second fluorescent image lu2 on the observation monitor 5 while maintaining the color balance between the reflection light images r1 and g1, or between the r2 and g2.

In the present embodiment, the threshold values for the white spot noise suppression may be appropriately set in accordance with the image pickup time set to the electronic endoscope 102A or 102B, thus effectively suppressing the white spot noise.

According to the present embodiment, in spite of the difference in characteristics of the excited light cut filters, quality fluorescent observation image may be obtained while suppressing the white spot noise appropriately.

In the aforementioned explanation, the multiplication factor of the CCD 25E for the fluorescent image pickup is set to be higher than that of the reflection light pickup image. Even if the multiplication factor is set to the same value in the case of the fluorescent image pickup and the reflection light image pickup, the threshold in accordance with the time for image picking up is used, resulting in the white scale noise suppression.

In the aforementioned explanation, if the first and the second electronic endoscopes 102A and 102B have different CCD 25E amplification factors, the white spot noise suppression may be done by using the threshold values set for the fluorescent image depending on the amplification factor.

In the aforementioned explanation, function of the white spot noise suppression circuit 111 is not used in the normal observation mode. Even in the normal observation mode, the white spot noise suppression may be performed using the threshold value set to be the value smaller than the one to be set for the fluorescent observation mode. The information with respect to the threshold value may be stored in the scope ID generation circuit 150. In the present embodiment, the white spot noise suppression is executed by the white spot noise suppression circuit 111 to the image pickup signal frame sequentially inputted. In the modified example shown in FIG. 31, the white spot noise suppression circuit 121 may execute the white spot noise suppression after synchronization in the synchronization circuit 45.

Figure 31:
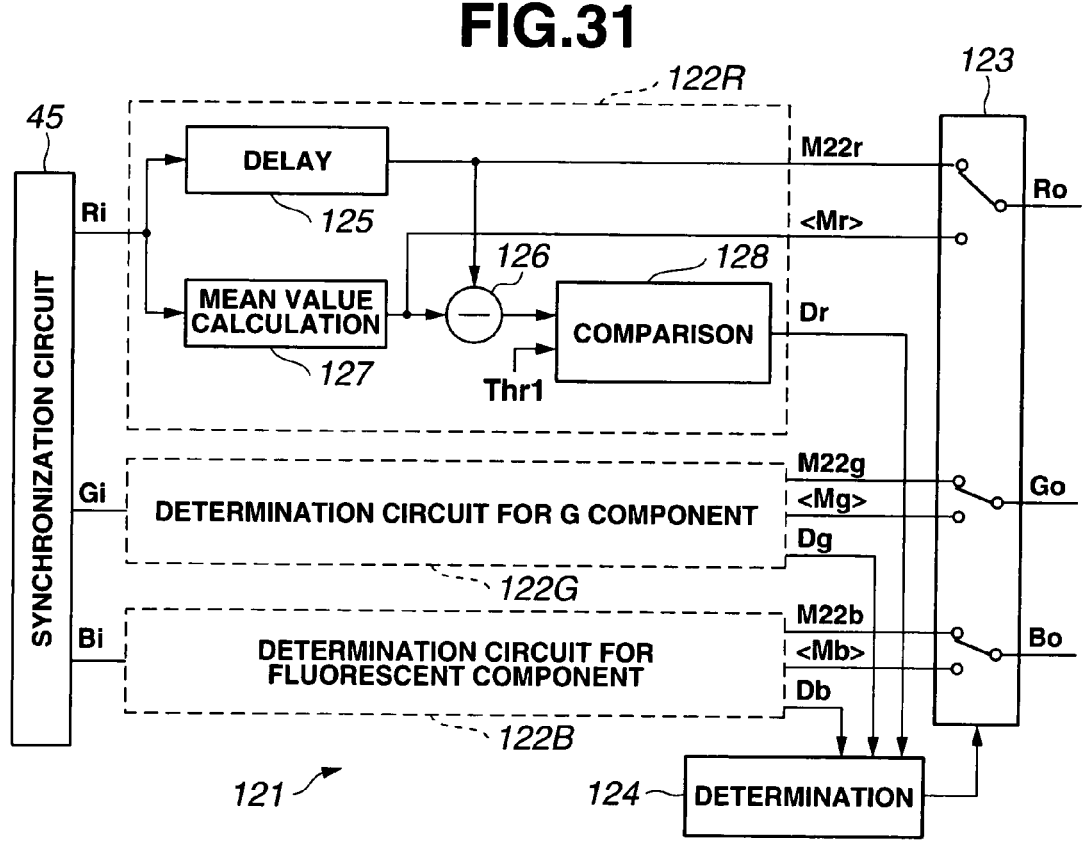
FIG. 31 is a view showing a configuration of a white spot suppression circuit in a modified example.

The white spot noise suppression circuit 121 in the modified example shown in FIG. 31 is formed by modifying the white spot noise suppression circuit 111 shown in FIG. 20 according to the fourth embodiment to the white spot noise suppression circuit 121 in the modified example shown in FIG. 23. However, they have basically the same configurations.

The white spot noise suppression circuit 121 shown in FIG. 31 is different from the white spot noise suppression circuit 121 in the point that the threshold value applied to the comparator 128 is controlled by the scope ID of the scope ID generation circuit 150. FIG. 31 shows the state where the first electronic endoscope 102A is connected. In this case, the threshold value Thr1 is applied to the comparator 128 of the R component determination circuit 122R.

The threshold value Thg1 is applied to the comparator 128 of the G component determination circuit 122Q which is not clearly shown. The threshold value Thb1 is applied to the comparator 128 of the fluorescent component (B component) determination circuit 122B.

The modified example provides substantially the same effects as in the case of the fifth embodiment.

The embodiment formed by partially combining the aforementioned embodiments belongs to the present invention.

INDUSTRIAL APPLICABILITY

Even in the case where the illumination light intensity is insufficient, for example, under the narrow band light observation with respect to the image in the body cavity picked up by the image pickup means in the endoscope, the image process may be executed for alleviating lowering of the contrast while effectively suppressing the noise. Accordingly, the endoscopic image suitable for the diagnosis may be displayed.

The present invention is filed based on Patent Application No. 2005-82544 filed in Japan on Mar. 22, 2005, claiming priority. The disclosed content is incorporated by reference in the specification, claims and the drawings herein.

The invention claimed is:
1. An image processor for executing an image processing of image data picked up by image pickup means, comprising:
   filter process means for filtering the image data with a plurality of spatial filters;
   brightness calculation means for calculating a brightness in a local area of the image data;
   weighting means for weighting an output of the filter process means in accordance with an output of the filter process means and/or an output of the brightness calculation means; and inverse filter process means for executing an inverse filtering with respect to an output of the weighting means to generate process image data wherein when the output of the filter process means is larger than a first predetermined value, the weighting means uses a first predetermined weighting coefficient irrespective of the output of the filter process means, and when the output of the filter process means is smaller than the first predetermined value, the weighting means changes the weighting coefficient to a further smaller value in accordance with the output of the filter process means;

when the output of the filter process means is smaller than a second predetermined value, the weighting means uses a second predetermined weighting coefficient in reference to the output of the filter process means in order to set the weighting coefficient to a level for effectively eliminating a noise contained in the output of the filter process means; and the first and second predetermined values are changed in accordance with an output of the brightness calculation means.

2. The image processor according to claim 1, further comprising weighted mean calculation means for calculating a weighted mean value of the image data and an output of the inverse filter process means in accordance with an output of the brightness calculation means.

3. The image processor according to claim 1, wherein the filter process means is an orthogonal transform process means using an orthogonal base, and the inverse filter process means is an inverse orthogonal transform process means.

4. The image processor according to claim 3, wherein the orthogonal base is a base of Karhunen-Loeve transform calculated with respect to predetermined image data.

5. The image processor according to claim 3, wherein the orthogonal base is a base of a discrete cosine transform.

6. The image processor according to claim 3, wherein the filter process means executes the filtering to the image data in a small area with n×n pixel to obtain pixel value of a center pixel in the small area using a filter number r smaller than the number of n×n where n is an odd number.

7. The image processor according to claim 6, wherein the filter process means defines filter coefficients by eigenvectors, respectively, and executes the filtering using the filter coefficients in descending order according to eigenvalues corresponding to the eigenvectors, up to an r-number of filter coefficient.

8. The image processor according to claim 1, wherein the filter process means executes the filtering of inputted image data to the image processor using a different filter coefficient corresponding to a color component of the inputted image data.

9. The image processor according to claim 1, wherein the filter process means executes the filtering of inputted image data using a filter coefficient common to different color components of the inputted image data.

10. The image processor according to claim 1, wherein the weighting means changes a weighting coefficient used for the weighting based on at least one of a gain value of an amplifier to be amplified in a process until the image data are inputted to the brightness calculation means, a type of the image pickup means, and a degree of correction with respect to a sharpness.

11. The image processor according to claim 1, wherein when the output of the filter process means is smaller than a predetermined value, the weighting means changes the predetermined value for applying a weighting coefficient of 0 irrespective of an output of the filter process means in accordance with an output of the brightness calculation means.

12. The image processor according to claim 1, wherein:

when the output of the filter process means is larger than a first predetermined value, the weighting means sets a weighting coefficient to 1 irrespective of the output of the filter process means, and when the output of the filter process means is smaller than a second predetermined value, the weighting means sets the weighting coefficient to 0 irrespective of the output of the filter process means;

when the output of the filter process means is a value between the first and the second predetermined values, the weighting means sets the weighting coefficient to a value between 0 and 1; and the first and the second predetermined values are changed in accordance with an output of the brightness calculation means.

13. An endoscope apparatus comprising:

an endoscope equipped with image pickup means;

filter process means for filtering of image data picked up by the image pickup means, to which a plurality of filters are applied;

brightness calculation means for calculating a brightness in a local area of the image data, weighting means for weighting an output of the filter process means in accordance with an output of the filter process means and/or an output value of the brightness calculation means; and inverse filter process means for executing an inverse filtering with respect to an output of the weighting means to obtain process image data wherein:

when the output of the filter process means is larger than a first predetermined value, the weighting means uses a first predetermined weighting coefficient irrespective of the output of the filter process means, and when the output of the filter process means is smaller than the first predetermined value, the weighting means changes the weighting coefficient to a further smaller value in accordance with the output of the filter process means;

when the output of the filter process means is smaller than a second predetermined value, the weighting means uses a second predetermined weighting coefficient in reference to the output of the filter process means in order to set the weighting coefficient to a level for effectively eliminating a noise contained in the output of the filter process means; and the first and second predetermined values are changed in accordance with an output of the brightness calculation means.

14. The endoscope apparatus according to claim 13, further comprising weighted mean calculation means for calculating a weighted mean value of the image data and an output of the inverse filter process means in accordance with an output of the brightness calculation means.

15. The endoscope apparatus according to claim 13, wherein the filter process means is an orthogonal transform process means using an orthogonal base, and the inverse filter process means is an inverse orthogonal transform process means.

16. The endoscope apparatus according to claim 15, wherein the orthogonal base is a base of Karhunen-Loeve transform calculated with respect to predetermined image data.

17. The endoscope apparatus according to claim 15, wherein the orthogonal base is a base of a discrete cosine transform.

18. The endoscope apparatus according to claim 15, wherein the filter process means executes the filtering to the image data in a small area with n×n pixel to obtain pixel value of a center pixel in the small area with a filter number r smaller than the number of n×n where n is an odd number.

19. The endoscope apparatus according to claim 18, wherein the filter process means defines filter coefficients by eigenvectors, respectively, and executes the filtering using the filter coefficients in descending order according to eigenvalues corresponding to the eigenvectors, up to an r-number of filter coefficient.

20. The endoscope apparatus according to claim 13, wherein the filter process means executes the filtering of inputted image data to the image processor using a different filter coefficient corresponding to a color component of the inputted image data.

21. The endoscope apparatus according to claim 13, wherein the filter process means executes the filtering of inputted image data using a filter coefficient common to different color components of the inputted image data.

22. The endoscope apparatus according to claim 13, wherein the weighting means changes a weighting coefficient used for the weighting based on at least one of a gain value of an amplifier to be amplified in a process until the image data are inputted to the brightness calculation means, a type of the image pickup means, and a degree of correction with respect to a sharpness.

23. The endoscope apparatus according to claim 13, wherein when the output of the filter process means is smaller than a predetermined value, the weighting means changes the predetermined value for applying a weighting coefficient of 0 irrespective of an output of the filter process means in accordance with an output of the brightness calculation means.

24. The endoscope apparatus according to claim 13, wherein:
when the output of the filter process means is larger than a first predetermined value, the weighting means sets a weighting coefficient to 1 irrespective of the output of the filter process means, and when the output of the filter process means is smaller than a second predetermined value, the weighting means sets the weighting coefficient to 0 irrespective of the output of the filter process means;
when the output of the filter process means is a value between the first and the second predetermined values, the weighting means sets the weighting coefficient to a value between 0 and 1; and
the first and the second predetermined values are changed in accordance with an output of the brightness calculation means.

* * * * *